US012582956B2

(12) United States Patent
     Feng

(10) Patent No.: US 12,582,956 B2
(45) Date of Patent: **\*Mar. 24, 2026**

(54) ARTICLES OF MANUFACTURE WITH POLYUREA CAPSULES CROSS-LINKED WITH CHITOSAN

(71) Applicant: Encapsys, LLC, Appleton, WI (US)

(72) Inventor: Linsheng Feng, Menasha, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/175,236

(22) Filed: Feb. 12, 2021

(65) Prior Publication Data

US 2021/0339217 A1     Nov. 4, 2021

Related U.S. Application Data

(63) Continuation-in-part of application No. 17/175,090, filed on Feb. 12, 2021, now Pat. No. 11,648,522.

(Continued)

(51) Int. Cl.
     *B01J 13/16*     (2006.01)
     *A61K 8/11*     (2006.01)
     (Continued)

(52) U.S. Cl.
     CPC ................. *B01J 13/16* (2013.01); *A61K 8/11* (2013.01); *A61K 8/87* (2013.01); *A61Q 5/12* (2013.01);
     (Continued)

(58) Field of Classification Search
     CPC ........ B01J 13/16; B01J 13/206; B01J 13/043; B01J 13/14; B01J 13/22; A61K 8/11; A61K 2800/654; A61K 2800/10; A61K 8/736; A61K 2039/55555; A61Q 5/12; A61Q 19/10; A61Q 19/00; C08L 67/02; C08L 71/00; C08L 79/08; C08L 2205/03; C08L 2310/00; C11D 3/3726; C11D 3/505; C11D 11/0017; C11D 17/0039; C11D 3/0015; C11D 3/227; A61L 15/28; A61L 15/46;

(Continued)

(56) References Cited

U.S. PATENT DOCUMENTS 4,138,362 A     2/1979   Vassiliades et al.
10,537,503 B2   1/2020   Lei et al.

(Continued)

OTHER PUBLICATIONS https://patents.google.com/patent/CN102258967A/en (Year: 2011).*

(Continued)

*Primary Examiner* — Angela C Brown-Pettigrew
*Assistant Examiner* — Preeti Kumar
(74) *Attorney, Agent, or Firm* — Daniel S. Ward

(57) ABSTRACT

Novel articles of manufacture are described based on a combination of an adjunct material and microcapsules made by an improved process. The improved microcapsules are chitosan urea and encapsulate a benefit agent. The process comprises combining an adjunct material formed of microcapsules formed by a water phase comprising hydrolyzing chitosan in an acidic medium at a pH of 6.5 or less for an extended period and combining with a polyisocyanate. The reaction product of the hydrolyzed chitosan and polyisocyanate yields a microcapsule having improved release characteristics, with enhanced degradation characteristics in OECD test method 301B.

23 Claims, 1 Drawing Sheet

Related U.S. Application Data

(60) Provisional application No. 63/005,574, filed on Apr. 6, 2020, provisional application No. 62/976,471, filed on Feb. 14, 2020.

(51) Int. Cl.

| | |
|---|---|
| *A61K 8/87* | (2006.01) |
| *A61L 15/28* | (2006.01) |
| *A61L 15/46* | (2006.01) |
| *A61Q 5/12* | (2006.01) |
| *A61Q 19/10* | (2006.01) |
| *B01J 13/20* | (2006.01) |
| *C08L 67/02* | (2006.01) |
| *C08L 71/00* | (2006.01) |
| *C08L 79/08* | (2006.01) |
| *C11D 3/00* | (2006.01) |
| *C11D 3/37* | (2006.01) |
| *C11D 3/50* | (2006.01) |
| *C11D 17/00* | (2006.01) |
| *C11D 17/04* | (2006.01) |

(52) U.S. Cl.
CPC ............ *A61Q 19/10* (2013.01); *B01J 13/206* (2013.01); *C08L 67/02* (2013.01); *C08L 71/00* (2013.01); *C08L 79/08* (2013.01); *C11D 3/001* (2013.01); *C11D 3/3726* (2013.01); *C11D 3/505* (2013.01); *C11D 17/0039* (2013.01); *C11D 17/047* (2013.01); *A61K 2800/654* (2013.01); *A61L 15/28* (2013.01); *A61L 15/46* (2013.01); *C08L 2205/03* (2013.01); *C08L 2205/20* (2013.01); *C08L 2310/00* (2013.01); *C11D 2111/12* (2024.01); *C11D 2111/14* (2024.01)

(58) Field of Classification Search
CPC .... A61L 2300/622; A61L 15/62; A61L 15/44; A61L 15/50; A61L 15/56; C08G 18/12; C08G 18/10; C08G 18/7664; C08G 18/3293; A23L 33/10; A23P 10/30; C09D 175/02; C11B 9/00; A01N 25/28
See application file for complete search history.

(56) References Cited

U.S. PATENT DOCUMENTS

| | | | | |
|---|---|---|---|---|
| 2004/0219268 A1* | 11/2004 | Hogoy | ................. | A23K 20/163 |
| | | | | 264/4.1 |
| 2013/0330292 A1 | 12/2013 | Lei et al. | | |
| 2017/0360676 A1* | 12/2017 | Dihora | ................. | A61K 8/0241 |
| 2018/0078507 A1* | 3/2018 | David | ................. | A61K 9/0095 |
| 2018/0085316 A1* | 3/2018 | Bleiel | ................. | A61K 38/28 |
| 2021/0252469 A1* | 8/2021 | Feng | ................. | B01J 13/16 |
| 2021/0339217 A1* | 11/2021 | Feng | ................. | C11D 17/0039 |

OTHER PUBLICATIONS

Practical examples of pH values, https://www.ctec-chemicals.com/en/tips-tricks/concept-ph#:~:text=Acetic%20acid%3A%20pH%203,Ammonia%3A%20pH%2011 (Year: 2015).*

Production of Vinegar from Oil-palm Wine Using Acetobacter Aceti Isolated from Rotten Banana Fruits, Onuorah, Samuel & Lina, Joson & Obika, Ifeanyi. (2016). Production of Vinegar from Oil-palm Wine Using Acetobacter Aceti Isolated from Rotten Banana Fruits. universal journal of biomedical engineering (Year: 2016).* pH of Common Acids and Bases, https://www.aqion.de/site/ph-of-common-acids (Year: 2021).* https://www.aropha.com/OECD-301B.html (Year: 2024).* pH in Acetic Acid (Year: 2020).*

Rojas, John, Juliana Madrigal, and Juliana Ortiz. "Effect of acid hydrolysis on tableting properties of chitin obtained from shrimp heads." Tropical Journal of Pharmaceutical Research 14.7 (2015): 1137-1144.

Younes, Islem, and Marguerite Rinaudo. "Chitin and chitosan preparation from marine sources. Structure, properties and applications." Marine drugs 13.3 (2015): 1133-1174.

Kasaai, Mohammad Reza, Joseph Arul, and Gérard Charlet. "Fragmentation of chitosan by acids." The Scientific World Journal 2013 (2013).

Groboillot, A. F., et al. "Membrane formation by interfacial cross-linking of chitosan for microencapsulation of Lactococcus lactis." Biotechnology and bioengineering 42.10 (1993): 1157-1163.

Xie, Kaili, et al. "Monodisperse microcapsules with controlled interfacial properties generated in microfluidic T-shape junction." CFM 2017-23ème Congrès Français de Mécanique. AFM, Maison de la Mécanique, 39/41 rue Louis Blanc-92400 Courbevoie, 201.

Quong D. et al. "Microencapulation within cross-linked chitosan membranes." Chitin Handbook, R.A.A. Muzzarelli and M.G. Peter, eds., European Chitin Society. (1997). 405-410.

PCT/US2021/018004, Aug. 11, 2022, International Preliminary Report on Patentability.

* cited by examiner

ARTICLES OF MANUFACTURE WITH POLYUREA CAPSULES CROSS-LINKED WITH CHITOSAN

CROSS-REFENCE TO RELATED APPLICATIONS

This application is a continuation-in-part of U.S. patent application Ser. No. 17/175,090 filed Feb. 12, 2021, and claims the benefit of U.S. Provisional Patent Application No. 63/005,574 filed Apr. 6, 2020, and claims the benefit of U.S. Provisional Patent Application No. 62/976,471 filed Feb. 14, 2020 each of which are incorporated by reference herein in their entirety.

FIELD OF THE INVENTION

This invention relates to capsule manufacturing processes and microcapsules produced by such processes, and more particularly to articles of manufacture made by combining novel microcapsules with an adjunct material.

DESCRIPTION OF THE RELATED ART

Various processes for microencapsulation, and exemplary methods and materials are set forth in Schwantes (U.S. Pat. No. 6,592,990), Nagai et al. (U.S. Pat. No. 4,708,924), Baker et al. (U.S. Pat. No. 4,166,152), Wojciak (U.S. Pat. No. 4,093,556), Matsukawa et al. (U.S. Pat. No. 3,965,033), Matsukawa (U.S. Pat. No. 3,660,304), Ozono (U.S. Pat. No. 4,588,639), Irgarashi et al. (U.S. Pat. No. 4,610,927), Brown et al. (U.S. Pat. No. 4,552,811), Scher (U.S. Pat. No. 4,285,720), Shioi et al. (U.S. Pat. No. 4,601,863), Kiritani et al. (U.S. Pat. No. 3,886,085), Jahns et al. (U.S. Pat. Nos. 5,596,051 and 5,292,835), Matson (U.S. Pat. No. 3,516,941), Chao (U.S. Pat. No. 6,375,872), Foris et al. (U.S. Pat. Nos. 4,001,140; 4,087,376; 4,089,802 and 4,100,103), Greene et al. (U.S. Pat. Nos. 2,800,458; 2,800,457 and 2,730,456), Clark (U.S. Pat. No. 6,531,156), Saeki et al. (U.S. Pat. Nos. 4,251,386 and 4,356,109), Hoshi et al. (U.S. Pat. No. 4,221,710), Hayford (U.S. Pat. No. 4,444,699), Hasler et al. (U.S. Pat. No. 5,105,823), Stevens (U.S. Pat. No. 4,197,346), Riecke (U.S. Pat. No. 4,622,267), Greiner et al. (U.S. Pat. No. 4,547,429), and Tice et al. (U.S. Pat. No. 5,407,609), among others and as taught by Herbig in the chapter entitled "Microencapsulation" in Kirk-Othmer Encyclopedia of Chemical Technology, V. 16, pages 438-463.

Each patent described throughout this application is incorporated herein by reference to the extent each provides guidance regarding microencapsulation processes and materials.

Jabs et al., U.S. Pat. No. 4,847,152 teaches microcapsules with polyurea walls. The wall is the reaction product of an aromatic isocyanate with an isocyanate reactive group. The isocyanate reactive group can include di- and polyamines such as N-hydroxyethylethylenediamine, ethylene-1,2-diamine.

Hotz et al., U.S. Pat. Pub. 2013/0089590 teaches a fragrance microcapsule with a polyurea wall. The shell in the reaction product of at least two difunctional isocyanates and a difunctional amine.

EP 1693104 Maruyyama discloses microcapsules having a polyurethane or polyurea wall obtained from polycondensation of a polyfunctional isocyanate with a polyfunctional amine.

U.S. Pat. No. 9,816,059 describes a polyurea capsule, the capsule encapsulating an oil core, where the polyurea is a reaction product of a polyfunctional isocyanate and a polyfunctional amine. The polyfunctional amine can include hexamethylene diamine and other amines including chitosan. Chitosan is mentioned as a stabilizing agent, as a polyfunctional amine, as a coating, without any guidance or example how to work with this difficult to handle material.

Chitosan is a polysaccharide and can be a difficult material to utilize in microencapsulation processes. Chitosan is generally insoluble in water above pH 7, and below about pH 6.5 is cationic. Chitosan is soluble in low pH acidic solutions such as hydrochloric acid, lactic acid, propionic acid, succinic acid, acetic acid, citric acid and phosphoric acid, forming a hard to handle viscous solution but generally insoluble in water above pH 7. At pH values below 4, the amino groups of chitosan promote electrostatic repulsion and the polymer swells. In acid solution the free amine groups are believed to form hydrogen bonds with adjacent oxygen groups.

The dissolved polysaccharide has positive charged $-NH_3^+$ groups and adheres to anionic surfaces. Chitosan forms aggregates with polyanions and chelates heavy metals.

A need exists in the art for polyurea type microcapsules having improved properties in terms of better deposition efficiency, lower leakage measured as lower free oil, and having cationic charge at pH less than about 7. If chitosan can be adapted to be useful as a solubilized cross-linker, an improved polyurea wall material becomes possible.

The present invention overcomes the above deficiencies of the present art by teaching an improved polyurea microcapsule cross-linked with chitosan. The chitosan is hydrolyzed to enable the chitosan to be soluble even at pH above 5, enabling its use in microencapsulation processes such as interfacial encapsulation.

Although the art generally mentions chitosan as a possible component in forming wall material in microencapsulation, there is little teaching as how to practically utilize this difficult to handle material.

Chitosan is generally insoluble in water, alkali and most organic solvents. Even under acidic low pH condition, solubility is generally less than 2 wt %. The composition is viscous, difficult to handle and requires considerable dilution. Chitosan concentrations less than 2 wt % make the material unsuitable for interfacial microencapsulation.

Chitosan is insoluble at higher pH and capsule formation under capsule forming conditions usually involves pH of 7 or 9 or even more alkaline conditions, presenting a situation where chitosan is an essentially insoluble viscous mass unsuitable for interfacial encapsulation.

A need exists for chitosan polyurea compositions at higher concentrations of chitosan which overcome the technical challenges of working with chitosan, and provide a useful concentration greater than 2 wt % in the water phase to enable successful chitosan urea polymer shell formation.

Although chitosan is mentioned as a cross-linker to prepare polyurea capsules such as in Lei et al., 2013/0330292, Lei does not provide any description how to employ chitosan. Chitosan is only soluble at low pH and not soluble at higher pH levels. As pH is increased, chitosan precipitates out of solution. Also, due to its high molecular weight, chitosan is an exceedingly difficult material to use as a cross-linker.

Bulgarelli et al., WO 2019063515 attempts to overcome the shortcomings of Lei by adding chitosan in solid form. Bulgarelli teaches adding chitosan in the water phase of the emulsion. Unprotonated chitosan is added once a reaction temperature of 80° C. is reached. The claims state the chitosan is added in solid form however, Bulgarelli provides no teaching in an example of how to effect dissolution of the solid chitosan. Chitosan is known to precipitate at alkaline pH's or even pH's exceeding 5.

Polyurea microcapsules have been described for certain applications as advantageous for being free of formaldehyde. Mechanical properties of polyurea systems described to date have not had core retention properties needed in certain challenging applications such as detergents, cleaners, compositions with surfactants, modifiers or other materials tending to negatively influence capsule performance upon prolonged storage. A polyurea chitosan that successfully incorporates chitosan at higher concentrations than heretofore achievable, that does not require additional cross-linkers, or that exhibits lower leakage would be an advance in the art. Improved shelf stability, lower leakage and degradability of such resultant compositions would be beneficial.

SUMMARY OF THE INVENTION

Figure 1:
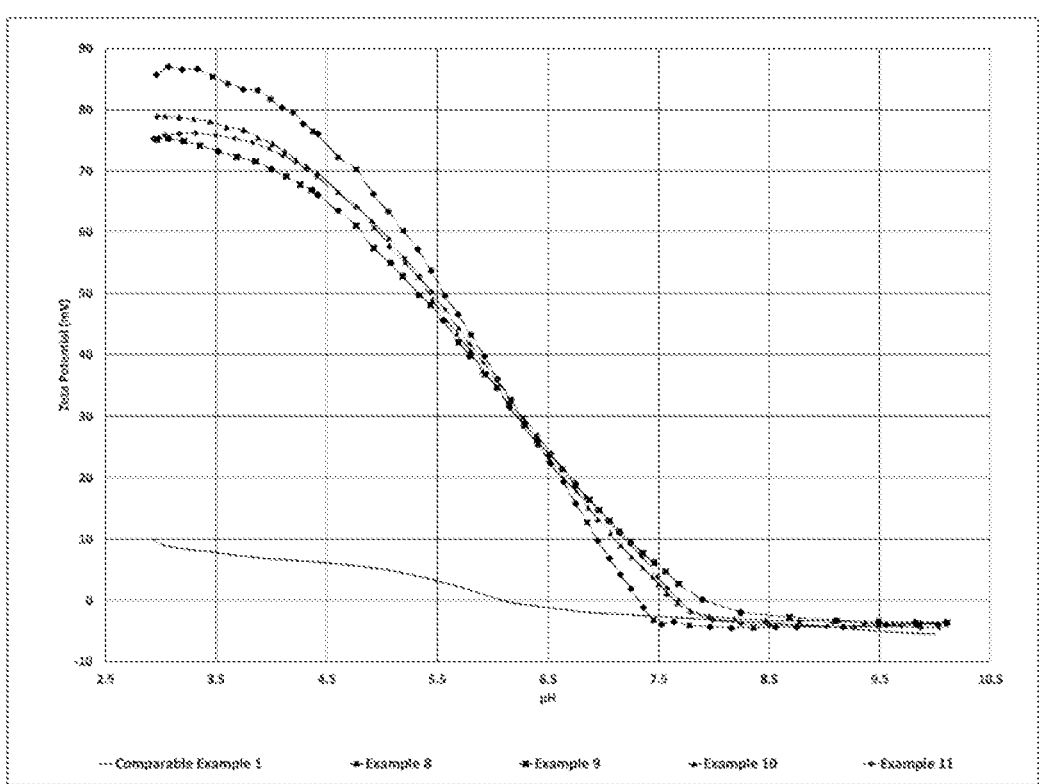
FIGS. 1 and 2 are graphs of zeta potential for microcapsules prepared according to the invention.
Figure 2:
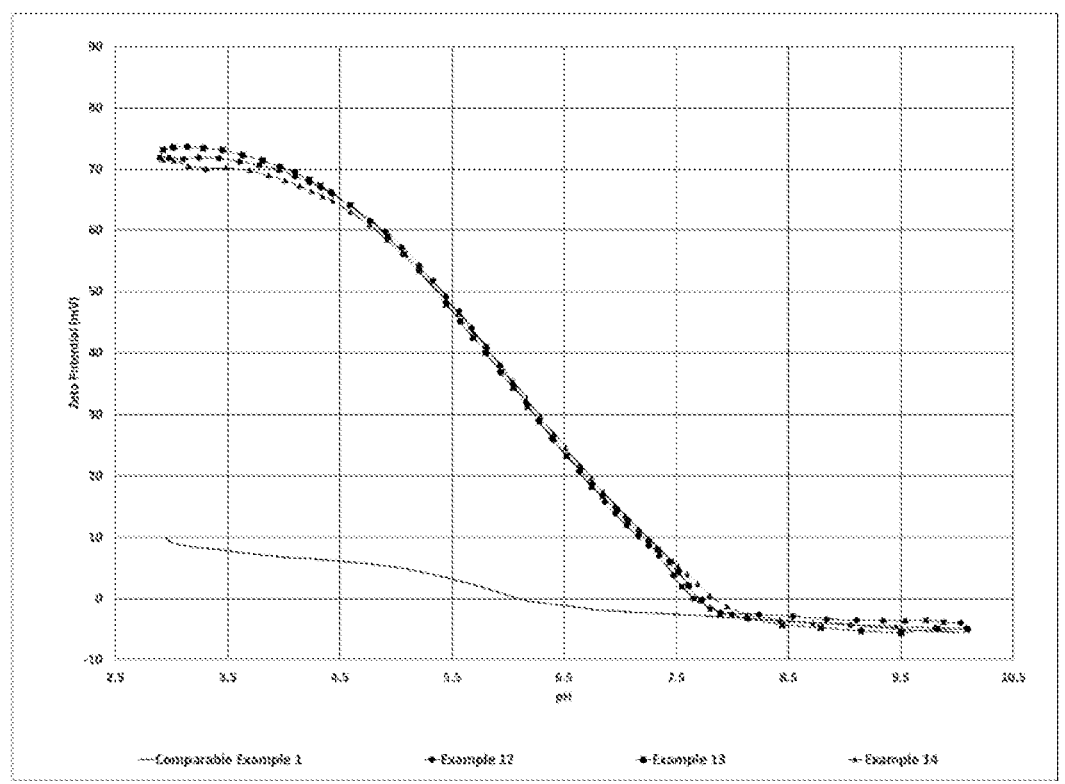

The invention describes a composition and process of forming a population of microcapsules comprising a core and a shell surrounding the core, the process comprising hydrolyzing chitosan in an acidic medium at a pH of 6.5 or less and a temperature of at least 60° C., for at least about one hour. A water phase of the hydrolyzed chitosan is formed by the above process. In addition, an oil phase is formed by dissolving or dispersing at least one benefit agent and at least one polyisocyanate into an oil phase. The benefit agent often can itself be the oil of the oil phase, with the polyisocyanate and benefit agent dissolved together, or optionally with an added oil. An emulsion is formed by mixing, under high shear agitation, the water phase and the oil phase into an excess of the water phase, thereby forming droplets of the oil phase and benefit agent dispersed in the water phase, with the droplets comprising the core of the core-shell microcapsule. Optionally, the pH of the emulsion can be adjusted in a range from pH 2 to pH 6.5. The emulsion is then cured by heating to at least 40° C., or even at least 60° C., for a time sufficient to form a shell at an interface of the droplets with the water phase, the shell is a polyurea comprising the reaction product of the polyisocyanate and hydrolyzed chitosan, the shell surrounding the droplets of the oil phase and benefit agent. For many applications a target droplet size is 0.1 to 80 microns, or even 0.5 to 50 microns.

In a further embodiment, the chitosan is first processed by being hydrolyzed at a pH of less than 6.5, such as a pH of from pH 3 to pH 6, and a temperature of at least 40° C., or even at least 60° C., or even at least 80° C. The hydrolysis time, depending on pH and temperature can be brief, but more typically would be at least one hour, or even for at least 24 hours. By such a processing step, the chitosan in the hydrolyzing step of any of the embodiments is deacetylated to at least 50% or even at least, 75%, or even to at least 80%, or even to at least 85%, or even at least 92%. Desirably, the chitosan in the hydrolyzing step can be depolymerized to an average size of 95 kilodaltons (kDa) or less. The shell formed is a polyurea and the reaction product of polyisocyanate comprising any of isocyanate monomer, oligomer or prepolymer and the hydrolyzed chitosan. The population of microcapsules can comprise an aqueous slurry, or alternatively can be sprayed onto a substrate, or alternatively spray-dried, resulting in a polyurea-chitosan shell with further chitosan deposited on the surface of the formed microcapsules. The unreacted chitosan in the aqueous slurry, if not decanted, can form the further chitosan deposited on the surface of the formed microcapsules.

In one embodiment, the microcapsules are dried and fracture upon drying, thereby releasing the core. This embodiment can find uses in cleaners with fragrance delivery or in agriculture with a benefit agent such as an agricultural active. Dry-pop type capsules, which fracture on drying, are formed through controlling reaction conditions such as controlling cure time and controlling temperature to yield capsules with thinner walls. Higher cure temperatures, along with longer cure times, can promote higher crosslinking density and enhanced brittleness. A thinner wall, such as from 0.1 nanometer to about 300 nanometers, tends to lend itself to becoming brittle on drying. Even in the dry-pop embodiment, the capsules of the invention exhibit lower leakage and better retention of the core in the capsule slurry pre-drying.

In certain embodiments the chitosan in the polyurea shell can be from 21 wt % to 85 wt % or even 90 wt % of the total shell as compared to the amount of polyisocyanate.

In a particular embodiment the process of the invention makes possible a polyurea shell of the core-shell microcapsule having chitosan in the polyurea shell (as compared to the amount of polyisocyanate) at 21 wt % of even greater, more particularly 21 wt % to 90 wt %, or even from 21 wt % to 85 wt %, or even 21 wt % to 75 wt %, or 21 wt % to 55 wt % of the total shell being chitosan.

The chitosan polyurea capsules of the invention in an alternative embodiment make possible forming a reacted polymer shell having a high proportion of chitosan moieties in the polymer. The chitosan to urea weight ratio of the polymer shell can be more than 21 wt % chitosan, or even 21 wt % to 40 wt % chitosan, or even 21 wt % to 60 wt % chitosan, or even 25 wt % to 80 wt % or even to 90 wt % chitosan. Such high weight percent proportions of chitosan in a chitosan polyurea microcapsule make possible an improved capsule system not previously achieved with interfacial type of encapsulation processes. The process and composition of the invention differ from ionic type of processes based on coacervation, as the polymer of the invention is covalently cross-linked with the polyurea constituent monomers, oligomers and prepolymers forming the chitosan polyurea polymer shell.

The composition comprises a core-shell microcapsule, the core comprising a benefit agent, the shell comprising a polyurea resin formed by the reaction of an isocyanate monomer, oligomer or prepolymer and a hydrolyzed chitosan. The chitosan is first hydrolyzed in an acidic medium at a pH of 6.5 or less and a temperature of at least 60° C., for at least one hour.

At low pH, the free amine in chitosan becomes protonated. Chitosan, for purposes hereof, is intended to encompass monomers, oligomers, prepolymers and polymers thereof. When chitosan becomes protonated, conventional understanding would be that chitosan loses the capability of acting as a cross-linker. Chitosan also ceases to act as an emulsifier at low pH, generally of less than pH 4.

A surprising aspect is that capsules formed, according to the invention at low pH, are not only tight capsules with low leakage at high wt % chitosan to urea (or polyisocyanate)

ratios, but that such capsules exhibit degradable properties in relatively short time periods. Microcapsules according to the invention are degradable as compared to capsules formed of the same or similar materials under different reaction conditions. Small differences in reaction conditions unexpectedly give rise to encapsulates with significantly different properties. The effect is more pronounced for reactions where in the chitosan hydrolyzation step, the pH is adjusted to around pH 4, or from pH 2-6, or from pH 3-5, but preferably from pH 3.5-5. For capsules made with chitosan that were hydrolyzed at pH 6 or above, the capsule shell showed minimum biodegradation according to the OECD 301 (B) method. However, the capsule shell degraded over 60% in 28 days when the capsule was made with chitosan hydrolyzed at pH 5 or less. Degradability increases as pH of hydrolysis is decreased below pH 6.

Chitosan in the capsule formation process of the invention is first hydrolyzed under acidic conditions (pH 6.5 or less). Optionally the chitosan is hydrolyzed at a pH of from 2 to 6.5, or even from a pH of from 4 to 6. This yields a deacetylated, depolymerized chitosan having water solubility, yet retaining an ability to act as an emulsifier or to replace the need for emulsifier, making additional emulsifiers optional.

The microcapsules according to the invention can be fashioned to have a zeta potential of at least 15 millivolts (mV) at a pH of 4.5, or even at least 40 mV at a pH of 4.5, or even at least 60 mV at a pH of 4.5 Such microcapsules are cationic and useful in applications where deposition onto anionic surfaces is desirable. At higher pH, the capsules can be made nonionic or anionic.

In one embodiment, the ratio of the isocyanate monomer, oligomer or prepolymer to hydrolyzed chitosan is up to 1:10 by weight. Chitosan as a percentage by weight of the polyisocyanate shell can be as little as 21% up to 95% of the shell. Based on total microcapsules weight, the shell can comprise at least 5% by weight of the core-shell microcapsule, or even at least 3% by weight, or even at least 1% by weight of the core-shell microcapsule, and up to 15% by weight of the core-shell microcapsule. The chitosan can have a degree of deacetylation of at least 75% or even at least 85%, or even at least 92%. The core-shell microcapsule, in certain embodiments, can have a ratio of core to shell up to about 99:1, or even 99.5:0.5 on the basis of weight. The benefit agent of the core-shell microcapsules can be selected from a fragrance, an agricultural active, a phase change material and other actives as described herein. The core-shell microcapsules typically have a mean particle size of from 1 to 100 microns. Different particle sizes are obtainable by controlling droplet size during emulsification.

The present invention teaches an article of manufacture made by a process comprising combining an adjunct material and microcapsules, the microcapsules comprising a core and a shell surrounding the core. The microcapsules are formed by a process comprising forming a water phase by hydrolyzing chitosan in an aqueous acidic medium at a pH of 6.5 or less and a temperature of at least 60° C. for at least one hour. An oil phase is formed comprising dissolving together at least one benefit agent and at least one polyisocyanate, optionally with an added oil. An emulsion is formed by mixing under high shear agitation the water phase and the oil phase into an excess of the water phase, thereby forming droplets of the oil phase and benefit agent dispersed in the water phase, and optionally adjusting the pH of the emulsion to be in a range from pH 2 to pH 6. The emulsion is cured by heating to at least 40° C., for a time sufficient to form a shell at an interface of the droplets with the water phase, the shell comprising the reaction product of the polyisocyanate and hydrolyzed chitosan, and the shell surrounding the core comprising the droplets of the oil phase and benefit agent.

The article of manufacture is formed by combining microcapsules with an adjunct material, wherein the adjunct material is selected from the group consisting of a carrier, a binder, an adhesive, a structurant, a surfactant, and a deposition aid. The article of manufacture can comprise a consumer product.

In certain embodiments the article of manufacture is selected from the group consisting of a soap, a surface cleaner, a laundry detergent, a fabric softener, a shampoo, a textile, a paper towel, an adhesive, a wipe, a diaper, a feminine hygiene product, a facial tissue, a pharmaceutical, a napkin, a deodorant, a heat sink, a foam, a pillow, a mattress, bedding, a cushion, a cosmetic, a medical device, packaging, an agricultural product, a cooling fluid, a wallboard, and an insulation.

In a particular embodiment the article of manufacture is formed of the combination with microcapsules described herein wherein the chitosan in capsule formation is hydrolyzed at a pH range from pH 2 to pH 6.5 and a temperature of at least 45° C. In a further embodiment the article of manufacture, wherein in capsule formation, the chitosan in the hydrolyzing step is deacetylated to at least 75%, or even at least 80%, or at least 85%, or even at least 92%. In addition, the chitosan in the hydrolyzing step is depolymerized to an average size of 95 kDa or less.

The shell formed is a chitosan polyurea, having a chitosan content of at least 21 wt % based on the weight of the shell. The article of manufacture formed of microcapsules wherein the population of microcapsules comprises an aqueous slurry having residual hydrolyzed chitosan in the slurry. The aqueous slurry can be spray dried, forming microcapsules overcoated with a layer of residual hydrolyzed chitosan deposited onto the microcapsules from the slurry. The ratio of hydrolyzed chitosan in the water phase as compared to the isocyanate in the oil phase is, based on weight, from 21:79 to 90:10, or even from 1:2 to 10:1, or even from 1:1 to 7:1.

In forming the article of manufacture the polyisocyanate can be selected from the group consisting of a polyisocyanurate of toluene diisocyanate, a trimethylol propane adduct of toluene diisocyanate and a trimethylol propane adduct of xylylene diisocyanate, methylene diphenyl isocyanate, toluene diisocyanate, tetramethylxylidene diisocyanate, naphthalene-1,5-diisocyanate, and phenylene diisocyanate. In one embodiment the article of manufacture can comprise microcapsules wherein the microcapsules are dried, and fracture upon drying, thereby releasing the core. In a further embodiment an article of manufacture is taught that comprises an adjunct material and a core-shell microcapsule, wherein the core comprises a benefit agent, and the shell comprises a polyurea resin, comprising the reaction product of a polyisocyanate and a chitosan. The chitosan is first hydrolyzed in an acidic medium at a pH of 6.5 or less, or even less than pH 6.5, or even at a pH of from 3 to 6, and a temperature of at least 60° C. for at least one hour. At least 21 wt % of the shell is comprised of moieties derived from the hydrolyzed chitosan and the shell degrades at least 40% in at least 14 days when tested according to test method OECD 301B.

In certain embodiments the article of manufacture has core-shell microcapsules, the shell comprising 1 to 15 percent by weight of the core-shell microcapsule. In a further embodiment the article of manufacture employs microcapsules made as described herein of polyisocyanate reacted with chitosan, wherein the polyisocyanate is selected from the group consisting of a polyisocyanurate of toluene diisocyanate, a trimethylol propane adduct of toluene diisocyanate, a trimethylol propane adduct of xylylene diisocyanate, methylene diphenyl isocyanate, toluene diisocyanate, tetramethylxylidene diisocyanate, naphthalene-1,5-diisocyanate, and phenylene diisocyanate.

In the article of manufacture described herein in certain embodiments, the shell of the microcapsules degrades at least 50% after at least 20 days when tested according to test method OECD 301B. In a particular embodiment the article of manufacture the microcapsules are formed of chitosan that has a degree of deacetylation of at least 50%. The core-shell microcapsule can have a ratio of core to shell up to 99:1, or even 99.5:1, on the basis of weight.

In a further embodiment of the article of manufacture a benefit agent is encapsulated, wherein the benefit agent is selected from the group consisting of perfume, fragrance, agricultural active, phase change material, essential oil, lubricant, colorant, preservative, antimicrobial active, antifungal active, herbicide, antiviral active, antiseptic active, antioxidant, biological active, deodorant, emollient, humectant, exfoliant, ultraviolet absorbing agent, corrosion inhibitor, silicone oil, wax, bleach particle, fabric conditioner, malodor reducing agent, dye, optical brightener, antiperspirant active and mixture thereof.

The core-shell microcapsules can have a mean particle size of from 1 to 100 microns and the microcapsule can be selected to be cationic.

Various articles of manufacture can be made according to the invention and can be selected from the group consisting of a soap, a surface cleaner, a laundry detergent, a fabric softener, a shampoo, a textile, a paper towel, an adhesive, a wipe, a diaper, a feminine hygiene product, a facial tissue, a pharmaceutical, a napkin, a deodorant, a heat sink, a foam, a pillow, a mattress, bedding, a cushion, a cosmetic, a medical device, packaging, an agricultural product, a cooling fluid, a wallboard, and an insulation. Other articles of manufacture arising from the combination of an adjunct material and the microcapsules can also be fashioned.

In certain embodiments the microcapsules have a zeta potential of at least 15 mV at a pH of 4.5. The microcapsules of the article of manufacture usefully results in a shell of the microcapsules which degrades at least 60% of its mass after at least 28 days when tested according to test method OECD 301B.

DETAILED DESCRIPTION

The present invention teaches an improved polyurea chitosan microcapsule. In the invention a polyurea microcapsule is successfully prepared by hydrolyzing chitosan in a first step and creating a water solution of the hydrolyzed chitosan. The hydrolyzed chitosan can be utilized at acidic to neutral pH as a cross-linker to form the shell of a core-shell microcapsule. A pH of at least 2 or even 3 or even at least 4 is useful for the water phase to facilitate cross-linking of the hydrolyzed chitosan with the isocyanate monomer.

In the invention, hydrolyzed chitosan is taught used as both crosslinker and emulsifier to prepare polyurea capsules. Hydrolyzing has the benefit of deacetylating and depolymerizing chitosan, thereby solubilizing an otherwise difficult to handle material. In the invention, chitosan is added into water in a jacketed reactor and at pH from 2 or even from 3 to 6.5, adjusted using acid such as concentrated HCl. The chitosan of this mixture is hydrolyzed by heating to elevated temperature, such as 85° C. in 60 minutes, and then held at this temperature from 1 minute to 1440 minutes or longer. The water phase is then cooled to 25° C. An oil phase is prepared by dissolving an isocyanate such as trimers of xylylene Diisocyanate (XDI) or polymers of methylene diphenyl isocyanate (MDI), in oil at 25° C. Diluents, for example isopropyl myristate, may be used to adjust the hydrophilicity of the oil phase. The oil phase is then added into the water phase and milled at high speed to obtain a targeted size. The emulsion is then cured in one or more heating steps, such as heating to 40° C. in 30 minutes and holding at 40° C. for 60 minutes. Times and temperatures are approximate. The temperature and time are selected to be sufficient to form and cure a shell at the interface of the droplets of the oil phase with the water continuous phase. For example, the emulsion is heated to 85° C. in 60 minutes and then held at 85° C. for 360 minutes to cure the capsules. The slurry is then cooled to room temperature.

The polyisocyanate useful in the invention is to be understood for purposes hereof as isocyanate monomer, isocyanate oligomer, isocyanate prepolymer, or dimer or trimer of an aliphatic or aromatic isocyanate. All such monomers, prepolymers, oligomers, or dimers or trimers of aliphatic or aromatic isocyanates are intended encompassed by the term "polyisocyanate" herein.

The polyisocyanate is an aliphatic or aromatic monomer, oligomer or prepolymer, usefully of two or more isocyanate functional groups. The polyisocyanate, for example, can be selected from aromatic toluene diisocyanate and its derivatives used in wall formation for encapsulates, or aliphatic monomer, oligomer or prepolymer, for example, hexamethylene diisocyanate and dimers or trimers thereof, or 3,3,5-trimethyl-5-isocyanatomethyl-1-isocyanato cyclohexane tetramethylene diisocyanate. The polyisocyanate can be selected from 1,3-diisocyanato-2-methylbenzene, hydrogenated MDI, bis(4-isocyanatocyclohexyl)methane, dicyclohexylmethane-4,4'-diisocyanate, and oligomers and prepolymers thereof. This listing is illustrative and not intended to be limiting of the polyisocyanates useful in the invention.

The polyisocyanates useful in the invention comprise isocyanate monomers, oligomers or prepolymers, or dimers or trimers thereof, having at least two isocyanate groups. Optimal cross-linking can be achieved with polyisocyanates having at least three functional groups.

Polyisocyanates, for purposes of the invention, are understood as encompassing any polyisocyanate having at least two isocyanate groups and comprising an aliphatic of aromatic moiety in the monomer, oligomer or prepolymer. If aromatic, the aromatic moiety can comprise a phenyl, a toluyl, a xylyl, a naphthyl or a diphenyl moiety, more preferably a toluyl or a xylyl moiety. Aromatic polyisocyanates, for purposes hereof, can include diisocyanate derivatives such as biurets and polyisocyanurates. The polyisocyanate, when aromatic, can be, but is not limited to, methylene diphenyl isocyanate, toluene diisocyanate, tetramethylxylidene diisocyanate, polyisocyanurate of toluene diisocyanate (commercially available from Bayer under the tradename Desmodur® RC), trimethylol propane-adduct of toluene diisocyanate (commercially available from Bayer under the tradename Desmodur® L75), or trimethylol propane-adduct of xylylene diisocyanate (commercially available from Mitsui Chemicals under the tradename Takenate® D-110N), naphthalene-1,5-diisocyanate, and phenylene diisocyanate.

Polyisocyanate, which is aliphatic, is understood as a polyisocyanate which does not comprise any aromatic moiety. There is a preference for aromatic polyisocyanate, however, aliphatic polyisocyanates and blends thereof are useful. Aliphatic polyisocyanates include a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100).

Core

The microcapsules of the present teaching include a benefit agent which comprises one or more ingredients that are intended to be encapsulated. The benefit agent is selected from a number of different materials such as chromogens and dyes, flavorants, perfumes, sweeteners, fragrances, oils, fats, pigments, cleaning oils, pharmaceuticals, pharmaceutical oils, perfume oils, mold inhibitors, antimicrobial agents, adhesives, phase change materials, scents, fertilizers, nutrients, and herbicides: by way of illustration and without limitation. The benefit agent and oil comprise the core. The core can be a liquid or a solid. With cores that are solid at ambient temperatures, the wall material can usefully enwrap less than the entire core for certain applications where availability of, for example, an agglomerate core is desired on application. Such uses can include scent release, cleaning compositions, emollients, cosmetic delivery and the like. Where the microcapsule core is phase change material, uses can include such encapsulated materials in mattresses, pillows, bedding, textiles, sporting equipment, medical devices, building products, construction products, HVAC, renewable energy, clothing, athletic surfaces, electronics, automotive, aviation, shoes, beauty care, laundry, and solar energy.

The core constitutes the material encapsulated by the microcapsules. Typically, particularly when the core material is a liquid material, the core material is combined with one or more of the compositions from which the internal wall of the microcapsule is formed or solvent for the benefit agent or partitioning modifier. If the core material can function as the oil solvent in the capsules, e.g. acts as the solvent or carrier for either the wall forming materials or benefit agent, it is possible to make the core material the major material encapsulated, or if the carrier itself is the benefit agent, can be the total material encapsulated. Usually however, the benefit agent is from 0.01 to 99 weight percent of the capsule internal contents, preferably 0.01 to about 65 by weight of the capsule internal contents, and more preferably from 0.1 to about 45% by weight of the capsule internal contents. With certain applications, the core material can be effective even at just trace quantities.

Where the benefit agent is not itself sufficient to serve as the oil phase or solvent, particularly for the wall forming materials, the oil phase can comprise a suitable carrier and/or solvent. In this sense, the oil is optional, as the benefit agent itself can at times be the oil. These carriers or solvents are generally an oil, preferably have a boiling point greater than about 80° C. and low volatility and are non-flammable. Though not limited thereto, they preferably comprise one or more esters, preferably with chain lengths of up to 18 carbon atoms or even up to 42 carbon atoms and/or triglycerides such as the esters of C6 to C12 fatty acids and glycerol. Exemplary carriers and solvents include, but are not limited to: ethyldiphenylmethane; isopropyl diphenylethane; butyl biphenyl ethane; benzylxylene; alkyl biphenyls such as propylbiphenyl and butylbiphenyl; dialkyl phthalates e.g. dibutyl phthalate, dioctylphthalate, dinonyl phthalate and ditridecylphthalate; 2,2,4-trimethyl-1,3-pentanediol diisobutyrate; alkyl benzenes such as dodecyl benzene; alkyl or aralkyl benzoates such as benzyl benzoate; diaryl ethers; di(aralkyl)ethers and aryl aralkyl ethers; ethers such as diphenyl ether, dibenzyl ether and phenyl benzyl ether; liquid higher alkyl ketones (having at least 9 carbon atoms); alkyl or aralkyl benzoates, e.g., benzyl benzoate; alkylated naphthalenes such as dipropylnaphthalene; partially hydrogenated terphenyls; high-boiling straight or branched chain hydrocarbons; alkaryl hydrocarbons such as toluene; vegetable and other crop oils such as canola oil, soybean oil, corn oil, sunflower oil, cottonseed oil, lemon oil, olive oil and pine oil; methyl esters of fatty acids derived from transesterification of vegetable and other crop oils, methyl ester of oleic acid, esters of vegetable oil, e.g. soybean methyl ester, straight chain paraffinic aliphatic hydrocarbons, and mixtures of the foregoing.

Useful benefit agents include perfume raw materials, such as alcohols, ketones, aldehydes, esters, ethers, nitriles, alkenes, fragrances, fragrance solubilizers, essential oils, phase change materials, lubricants, colorants, cooling agents, preservatives, antimicrobial or antifungal actives, herbicides, antiviral actives, antiseptic actives, antioxidants, biological actives, deodorants, emollients, humectants, exfoliants, ultraviolet absorbing agents, self-healing compositions, corrosion inhibitors, sunscreens, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, dyes, brighteners, antibacterial actives, antiperspirant actives, cationic polymers and mixtures thereof. Phase change materials useful as benefit agents can include, by way of illustration and not limitation, paraffinic hydrocarbons having 13 to 28 carbon atoms, various hydrocarbons such n-octacosane, n-heptacosane, n-hexacosane, n-pentacosane, n-tetracosane, n-tricosane, n-docosane, n-heneicosane, n-eicosane, n-nonadecane, octadecane, n-heptadecane, n-hexadecane, n-pentadecane, n-tetradecane, n-tridecane. Phase change materials can alternatively, optionally in addition include crystalline materials such as 2,2-dimethyl-1,3-propanediol, 2-hydroxymethyl-2-methyl-1, 3-propanediol, acids of straight or branched chain hydrocarbons such as eicosanoic acid and esters such as methyl palmitate, fatty alcohols and mixtures thereof.

Other useful benefit agents or core materials include sensates, silicone oils, waxes, lipids, skin coolants, vitamins, sunscreens, antioxidants, glycerine, catalysts, bleach particles, silicon dioxide particles, odor-controlling materials, antistatic agents, softening agents, insect repelling agents, colorants, antioxidants, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, anti-wear agents, anti-pilling agents, defoamers and anti-foaming agents, sun fade inhibitors, anti-allergenic agents, enzymes, water proofing agents, fabric comfort agents, shrinkage resistance agents, stretch resistance agents, stretch recovery agents, skin care agents, glycerin, and natural actives such as aloe vera, vitamin E, shea butter, cocoa butter, and the like, brighteners, antibacterial actives, antiperspirant actives, cationic polymers, dyes and mixtures thereof.

Preferably, in the case of fragrances, a perfume oil acts as benefit agent and solvent for the wall forming material, as illustrated in the examples herein.

The invention makes possible tailored surface charge of chitosan urea-based microcapsules by chemical attachment on the surface, especially the external surface of the microcapsule, through the charged domains or charged pendant groups of the resulting polymer.

Optionally the water phase may include an emulsifier. Non-limiting examples of emulsifiers include water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly (styrene sulfonate), isobutylene-maleic anhydride copolymer, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinyl benzenesulfonic acid or 2-acrylamido-2-methylpropanesulfonic acid homopolymers and copolymers, and partial amide or partial ester of such polymers and copolymers, carboxy modified polyvinyl alcohol, sulfonic acid-modified polyvinyl alcohol and phosphoric acid-modified polyvinyl alcohol, phosphated or sulfated tristyrylphenol ethoxylates, palmitamidopropyltrimonium chloride (Varisoft PATC™, available from Degussa Evonik, Essen, Germany), distearyl dimonium chloride, cetyltrimethylammonium chloride, quaternary ammonium compounds, fatty amines, aliphatic ammonium halides, alkyldimethylbenzylammonium halides, alkyldimethylethylammonium halides, polyethyleneimine, poly(2-dimethylamino)ethyl methacrylate) methyl chloride quaternary salt, poly(I-vinylpyrrolidone-co-2-dimethylaminoethyl methacrylate), poly(acrylamide-co-diallyldimethylammonium chloride), poly (allylamine), poly[bis(2-chloroethyl) ether-alt-1,3-bis[3-(dimethylamino)propyl]urea] quaternized, and poly (dimethylamine-co-epichlorohydrin-co-ethylenediamine), condensation products of aliphatic amines with alkylene oxide, quaternary ammonium compounds with a long-chain aliphatic radical, e.g. distearyldiammonium chloride, and fatty amines, alkyldimethylbenzylammonium halides, alkyldimethylethylammonium halides, polyalkylene glycol ether, condensation products of alkyl phenols, aliphatic alcohols, or fatty acids with alkylene oxide, ethoxylated alkyl phenols, ethoxylated aryl phenols, ethoxylated polyaryl phenols, carboxylic esters solubilized with a polyol, polyvinyl alcohol, polyvinyl acetate, or copolymers of polyvinyl alcohol polyvinyl acetate, polyacrylamide, poly(N-isopropylacrylamide), poly(2-hydroxypropyl methacrylate), poly(-ethyl-2-oxazoline), poly(2-isopropenyl-2-oxazoline-co-methyl methacrylate), poly(methyl vinyl ether), and polyvinyl alcohol-co-ethylene), and cocoamidopropyl betaine. Emulsifier, if employed, is typically from about 0.1 to 40% by weight, preferably 0.2 to about 15% by weight, more typically 0.5 to 10% be weight, based on total weight of the formulation The microcapsules may encapsulate a partitioning modifier in addition to the benefit agent. Non-limiting examples of partitioning modifiers include isopropyl myristate, mono-, di-, and tri-esters of $C_4$-$C_{24}$ fatty acids, castor oil, mineral oil, soybean oil, hexadecanoic acid, methyl ester isododecane, isoparaffin oil, polydimethylsiloxane, brominated vegetable oil, and combinations thereof. Microcapsules may also have varying ratios of the partitioning modifier to the benefit agent so as to make different populations of microcapsules that may have different bloom patterns. Such populations may also incorporate different perfume oils so as to make populations of microcapsules that display different bloom patterns and different scent experiences. US 2011-0268802 discloses other non-limiting examples of partitioning modifiers and is hereby incorporated by reference.

in the formation of the chitosan microcapsules, the aqueous solution contains a residual quantity of the hydrolyzed chitosan. This provides the option of dewatering the microcapsules such as through decanting, filtration, centrifuging or other separation technique. Alternatively, the aqueous slurry of chitosan polyurea microcapsules can be spray dried forming chitosan polyurea microcapsules further coated with a layer of the residual hydrolyzed chitosan from the water phase.

In one embodiment, the formed slurry of microcapsules can be further dispersed in additional water or with low concentration of residual overcoating hydrolyzed chitosan yielding chitosan polyurea microcapsules that can fracture upon drying, providing an additional release mechanism useful in some applications such as fragrance delivery or with agricultural actives for targeted delivery.

In some examples of the process and compositions, the microcapsules may consist of one or more distinct populations. The composition may have at least two different populations of microcapsules that vary in the exact make-up of the perfume oil and in the median particle size and/or partitioning modifier to perfume oil (PM:PO) weight ratio. In some examples, the composition includes more than two distinct populations that vary in the exact make up the perfume oil and in their fracture strengths. In some further examples, the populations of microcapsules can vary with respect to the weight ratio of the partitioning modifier to the perfume oil(s). In some examples, the composition can include a first population of microcapsules having a first ratio that is a weight ratio of from 2:3 to 3:2 of the partitioning modifier to a first perfume oil and a second population of microcapsules having a second ratio that is a weight ratio of less than 2:3 but greater than 0 of the partitioning modifier to a second perfume oil.

In some embodiments, each distinct population of microcapsules is preparable in a distinct slurry. For example, the first population of microcapsules can be contained in a first slurry and the second population of microcapsules contained in a second slurry. It is to be appreciated that the number of distinct slurries for combination is without limit and a choice of the formulator such that 3, 10, or 15 distinct slurries may be combined. The first and second populations of microcapsules may vary in the exact make up the perfume oil and in the median particle size and/or PM:PO weight ratio.

In some embodiments, the composition, can be prepared by combining the first and second slurries with at least one adjunct ingredient and optionally packaged in a container. In some examples, the first and second populations of microcapsules can be prepared in distinct slurries and then spray dried to form a particulate. The distinct slurries may be combined before spray drying, or spray dried individually and then combined together when in particulate powder form. Once in powder form, the first and second populations of microcapsules may be combined with an adjunct ingredient to form the composition useful as a feedstock for manufacture of consumer, industrial, medical or other goods. In some examples, at least one population of microcapsules is spray dried and combined with a slurry of a second population of microcapsules. In some examples, at least one population of microcapsules is dried, prepared by spray drying, fluid bed drying, tray drying, or other such drying processes that are available.

In some examples, the slurry or dry particulates can include one or more adjunct materials such as processing aids selected from the group consisting of a carrier, an aggregate inhibiting material, a deposition aid, a particle suspending polymer, and mixtures thereof. Non-limiting examples of aggregate inhibiting materials include salts that can have a charge-shielding effect around the particle, such as magnesium chloride, calcium chloride, magnesium bromide, magnesium sulfate, and mixtures thereof. Non-limiting examples of particle suspending polymers include polymers such as xanthan gum, carrageenan gum, guar gum, shellac, alginates, chitosan; cellulosic materials such as carboxymethyl cellulose, hydroxypropyl methyl cellulose, cationically charged cellulosic materials; polyacrylic acid; polyvinyl alcohol; hydrogenated castor oil; ethylene glycol distearate; and mixtures thereof.

In some embodiments, the slurry can include one or more processing aids, selected from the group consisting of water, aggregate inhibiting materials such as divalent salts; particle suspending polymers such as xanthan gum, guar gum, carboxy methyl cellulose.

In other examples of the invention, the slurry can include one or more carriers selected from the group consisting of polar solvents, including but not limited to, water, ethylene glycol, propylene glycol, polyethylene glycol, glycerol; non-polar solvents, including but not limited to, mineral oil, perfume raw materials, silicone oils, hydrocarbon paraffin oils, and mixtures thereof.

In some examples, said slurry may include a deposition aid that may comprise a polymer selected from the group comprising: polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinyl formamide, polyvinyl alcohol; polyvinyl alcohol cross-linked with boric acid; polyacrylic acid; polyglycerol ether silicone cross-polymers; polyacrylic acids, polyacrylates, copolymers of polyvinylamine and polyvinylalcohol oligomers of amines, in one aspect a diethylenetriamine, ethylene diamine, bis(3-aminopropyl)piperazine, N,N-Bis-(3-aminopropyl)methylamine, tris(2-aminoethyl)amine and mixtures thereof; polyethyleneimine, a derivatized polyethyleneimine, in one aspect an ethoxylated polyethyleneimine; a polymeric compound comprising, at least two moieties selected from the moieties consisting of a carboxylic acid moiety, an amine moiety, a hydroxyl moiety, and a nitrile moiety on a backbone of polybutadiene, polyisoprene, polybutadiene/styrene, polybutadiene/acrylonitrile, carboxyl-terminated polybutadiene/acrylonitrile or combinations thereof; pre-formed coacervates of anionic surfactants combined with cationic polymers; polyamines and mixtures thereof.

In some additional examples to illustrate the invention, at least one population of microcapsules can be contained in an agglomerate and then combined with a distinct population of microcapsules and at least one adjunct material. Said agglomerate may comprise materials selected from the group consisting of silicas, citric acid, sodium carbonate, sodium sulfate, sodium chloride, and binders such as sodium silicates, modified celluloses, polyethylene glycols, polyacrylates, polyacrylic acids, zeolites and mixtures thereof.

Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.).

Procedure for Determination of % Degradation

% degradation is determined by the "OECD Guideline for Testing of Chemicals" 301B $CO_2$ Evolution (Modified Sturm Test), adopted 17 Jul. 1992. For ease of reference, this test method is referred to herein as test method OECD 301B Procedure for Determination of Free Oil This method measures the amount of oil in the water phase and uses as an internal standard solution 1 mg/ml dibutyl phthalate (DBP)/hexane.

Weigh a little more than 250 mgs of DBP into a small beaker and transfer to a 250 ml volumetric rinsing the beaker thoroughly. Fill with hexane to 250 ml.

Sample Prep: Weigh approximately 1.5-2 grams (40 drops) of the capsule slurry into a 20 ml scintillation vial and add 10 ml's of the ISTD solution, cap tightly. Shaking vigorously several times over 30 minutes, pipette solution into an autosampler vial and analyze by GC.

Additional details. Instrumentation: HP5890 GC connected to HP Chem Station Software; Column: 5 m×0.32 mm id with 1 μm DB-1 liquid phase; Temperature 50 deg for 1 minute then heat to 320 deg @15 deg/min; Injector: 275° C.; Detector: 325° C.; 2 ul injection.

Calculation: Add total peak area minus the area for the DBP for both the sample and calibration. Calculate mg of free core oil:

$$\frac{\text{Total area from sample}}{\text{Total area from calibration}} \times \text{mg of oil in calibration solution} =$$
$$\text{mg of free oil}$$

Calculate % Free Core Oil $$\frac{\text{mg of free core oil}}{\text{Sample wt. (mg)}} \times 100 = \% \text{ free core oil in wet slurry}$$

Procedure for Determination of Benefit Agent Leakage

Obtain 2, one gram samples of benefit agent particle composition. Add 1 gram (Sample 1) of particle composition to 99 grams of product matrix in which the particle will be employed. Age the particle containing product matrix (Sample 1) for 2 weeks at 35° C. in a sealed glass jar. The other 1 gram sample (Sample 2) is similarly aged.

After 2 weeks, use filtration to recover the particle composition's particles from the product matrix (Sample 1) and from the particle composition (Sample 2). Treat each particle sample with a solvent that will extract all the benefit agent from each samples' particles. Inject the benefit agent containing solvent from each sample into a Gas Chromatograph and integrate the peak areas to determine the total quantity of benefit agent extracted from each sample.

Determine the percentage of benefit agent leakage by calculating the difference in the values obtained for the total quantity of benefit agent extracted from Sample 2 minus Sample 1, expressed as a percentage of the total quantity of benefit agent extracted from Sample 2, as represented in the equation below:

$$\text{Percentage of Benefit Agent Leakage} = \left(\frac{\text{Sample 2} - \text{Sample 1}}{\text{Sample 2}}\right) \times 100$$

Polyurea capsules prepared with chitosan exhibit positive zeta potentials as shown in FIG. 1. Such capsules have improved deposition efficiency on fabrics.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

In the following examples, the abbreviations correspond to the materials listed in Table 1.

TABLE 1

| Trade Name | Company/City | Material |
| --- | --- | --- |
| Selvol 540 | Sekisui Specialty Chemicals, Dallas, TX | Polyvinyl alcohol |
| ChitoClear | Primex EHF, Siglufjordur, Iceland | chitosan |
| Takenate D-110N | Mitsui Chemicals America, Inc., Rye Brook, NY | aliphatic polyisocyanate prepolymer |
| Mondur MR | Covestro LLC, Pittsburgh, PA | Polymeric diphenyl methane diisocyanate |
| SAS-305 | JX Nippon Chemical Texas Inc., Pasadena, TX | isopropyl diphenylethane |

COMPARATIVE EXAMPLE 1

An aqueous phase one is prepared by mixing 86.40 g 5% Selvol 540 in 273.60 g deionized water. The oil phase is prepared by mixing 159.38 g perfume oil and 23.91 g isopropyl myristate together and then dissolving 4.0 g Takenate D-110N into it with mixing. A water phase two is prepared by mixing 0.38 g diethylenetriamine in 25.00 g water. An emulsion is formed by mixing the oil phase into water phase one and milling to obtain a target particle size. Water phase two is then added to the emulsion which is then heated to 40° C. in 30 mins and held for 60 mins. The emulsion is then heated to 85° C. and maintained at this temperature for 6 hours with mixing. The free oil of the final slurry is 4.068%.

COMPARATIVE EXAMPLE 2

A water phase is prepared by dispersing 20.66 g ChitoClear into 439.00 g water while mixing in a jacketed reactor. The pH of the water phase is then adjusted to 2.61 using concentrated HCl under agitation. The water phase temperature is then increased to 85° C. over 60 minutes and then held at 85° C. for a period of time to hydrolyze the ChitoClear. The water phase temperature is then reduced to 25° C. after the hydrolyzing step over a period of 90 minutes. An oil phase is prepared by mixing 139.58 g perfume oil and 23.91 g isopropyl myristate together along with 4.00 g Takenate D-110N at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. No capsules are formed at this pH condition.

EXAMPLE 3

A water phase is prepared by dispersing 12.40 g ChitoClear into 350.00 g water while mixing in a jacketed reactor. The pH of the water phase is then adjusted to 4.7 using concentrated HCl under agitation. The water phase temperature is then increased to 85° C. over 60 minutes and then held at 85° C. fora period of time to hydrolyze the ChitoClear. The water phase temperature is then reduced to 25° C. after the hydrolyzing step over a period of 90 minutes. An oil phase is prepared by mixing 87.50 g perfume oil and 22.50 g isopropyl myristate together along with 15.00 g Takenate D-110N at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a free oil of 0.090% and a one week leakage of 3.604%.

EXAMPLE 4

A water phase is prepared by dispersing 12.40 g ChitoClear into 350.00 g water while mixing in a jacketed reactor. The pH of the water phase is then adjusted to 5.0 using concentrated HCl under agitation. The water phase temperature is then increased to 85° C. over 60 minutes and then held at 85° C. fora period of time to hydrolyze the ChitoClear. The water phase temperature is then reduced to 25° C. after the hydrolyzing step over a period of 90 minutes. An oil phase is prepared by mixing 159.38 g perfume oil and 23.91 g isopropyl myristate together along with 15.00 g Takenate D-110N at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a free oil of 0.088% and a one week leakage of 2.918%.

EXAMPLE 5

A water phase is prepared by dispersing 12.40 g ChitoClear into 350.00 g water while mixing in a jacketed reactor.

The pH of the water phase is then adjusted to 5.5 using concentrated HCl under agitation. The water phase temperature is then increased to 85° C. over 60 minutes and then held at 85° C. for a period of time to hydrolyze the ChitoClear. The water phase temperature is then reduced to 25° C. after the hydrolyzing step over a period of 90 minutes. An oil phase is prepared by mixing 159.38 g perfume oil and 23.91 g isopropyl myristate together along with 15.00 g Takenate D-110N at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a free oil of 0.043% and a one week leakage of 2.009%.

EXAMPLE 6

A water phase is prepared by dispersing 12.40 g Chito-Clear into 350.00 g water while mixing in a jacketed reactor. The pH of the water phase is then adjusted to 6.1 using concentrated HCl under agitation. The water phase temperature is then increased to 85° C. over 60 minutes and then held at 85° C. for a period of time to hydrolyze the Chito-Clear. The water phase temperature is then reduced to 25° C. after the hydrolyzing step over a period of 90 minutes. An oil phase is prepared by mixing 159.38 g perfume oil and 23.91 g isopropyl myristate together along with 15.00 g Takenate D-110N at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a free oil of 0.111% and a one week leakage of 1.909%.

EXAMPLE 7

A water phase is prepared by dispersing 12.40 g Chito-Clear into 350.00 g water while mixing in a jacketed reactor. The pH of the water phase is then adjusted to 6.0 using concentrated HCl under agitation. The water phase temperature is then increased to 85° C. over 60 minutes and then held at 85° C. for a period of time to hydrolyze the Chito-Clear. The water phase temperature is then reduced to 25° C. after the hydrolyzing step over a period of 90 minutes. An oil phase is prepared by mixing 159.38 g perfume oil and 23.91 g isopropyl myristate together along with 15.00 g Takenate D-110N at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a free oil of 0.076% and a one week leakage of 1.112%.

EXAMPLE 8

A water phase is prepared by dispersing 26.45 g Chito-Clear into 450.00 g water while mixing in a jacketed reactor. The pH of the water phase is then adjusted to 6.0 using concentrated HCl under agitation. The water phase temperature is then increased to 85° C. over 60 minutes and then held at 85° C. for a period of time to hydrolyze the Chito- Clear. The water phase temperature is then reduced to 25° C. after the hydrolyzing step over a period of 90 minutes. An oil phase is prepared by mixing 159.38 g perfume oil and 23.91 g isopropyl myristate together along with 4.00 g Takenate D-110N at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a free oil of 0.674% and a one week leakage of 41.930%.

EXAMPLE 9

A water phase is prepared by dispersing 12.40 g Chito-Clear into 350.00 g water while mixing in a jacketed reactor. The pH of the water phase is then adjusted to 6.0 using concentrated HCl under agitation. The water phase temperature is then increased to 85° C. over 60 minutes and then held at 85° C. for a period of time to hydrolyze the Chito-Clear. The water phase temperature is then reduced to 25° C. after the hydrolyzing step over a period of 90 minutes. An oil phase is prepared by mixing 159.38 g perfume oil and 23.91 g isopropyl myristate together along with 4.00 g Takenate D-110N at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a free oil of 0.272% and a one week leakage of 13.222%.

EXAMPLE 10

A water phase is prepared by dispersing 20.66 g Chito-Clear into 439.00 g water while mixing in a jacketed reactor. The pH of the water phase is then adjusted to 6.0 using concentrated HCl under agitation. The water phase temperature is then increased to 85° C. over 60 minutes and then held at 85° C. for a period of time to hydrolyze the ChitoClear. The water phase temperature is then reduced to 25° C. after the hydrolyzing step over a period of 90 minutes. An oil phase is prepared by mixing 159.38 g perfume oil and 23.91 g isopropyl myristate together along with 4.00 g Takenate D-110N at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a free oil of 0.304% and a one week leakage of 17.454%.

EXAMPLE 11

A water phase is prepared by dispersing 20.66 g Chito-Clear into 439.00 g water while mixing in a jacketed reactor. The pH of the water phase is then adjusted to 3.8 using concentrated HCl under agitation. The water phase temperature is then increased to 85° C. over 60 minutes and then held at 85° C. for a period of time to hydrolyze the ChitoClear. The water phase temperature is then reduced to 25° C. after the hydrolyzing step over a period of 90 minutes. An oil phase is prepared by mixing 159.38 g perfume oil and 23.91 g isopropyl myristate together along with 4.00 g Takenate D-110N at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a one week leakage of 28.204%.

EXAMPLE 12

A water phase is prepared by dispersing 20.66 g Chito-Clear into 439.00 g water while mixing in a jacketed reactor. The pH of the water phase is then adjusted to 4.2 using concentrated HCl under agitation. The water phase temperature is then increased to 85° C. over 60 minutes and then held at 85° C. fora period of time to hydrolyze the Chito-Clear. The water phase temperature is then reduced to 25° C. after the hydrolyzing step over a period of 90 minutes. An oil phase is prepared by mixing 159.38 g perfume oil and 23.91 g isopropyl myristate together along with 4.00 g Takenate D-110N at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a one week leakage of 24.174%.

EXAMPLE 13

A water phase is prepared by dispersing 20.66 g Chito-Clear into 439.00 g water while mixing in a jacketed reactor. The pH of the water phase is then adjusted to 4.9 using concentrated HCl under agitation. The water phase temperature is then increased to 85° C. over 60 minutes and then held at 85° C. fora period of time to hydrolyze the Chito-Clear. The water phase temperature is then reduced to 25° C. after the hydrolyzing step over a period of 90 minutes. An oil phase is prepared by mixing 159.38 g perfume oil and 23.91 g isopropyl myristate together along with 4.00 g Takenate D-110N at room temperature. The oil phase is added to the water phase under high shear milling to obtain an emulsion. The emulsion is heated to 40° C. over 30 minutes and held for 60 minutes. pH of the emulsion was then adjusted to 2.97 using hydrochloric acid. The emulsion is then heated to 85° C. and maintained at this temperature for 6 hours while mixing. The capsules formed at this pH condition had a one week leakage of 76.182%.

EXAMPLE 14

A water phase is prepared by dispersing 20.66 g Chito-Clear into 439.00 g water while mixing in a jacketed reactor. The pH of the water phase is then adjusted to 4.7 using concentrated HCl under agitation. The water phase temperature is then increased to 85° C. over 60 minutes and then held at 85° C. for a period of time to hydrolyze the ChitoClear. The water phase temperature is then reduced to 25° C. after the hydrolyzing step over a period of 90 minutes. An oil phase is prepared by mixing 159.38 g perfume oil and 23.91 g isopropyl myristate together along with 4.00 g Takenate D-110N at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a free oil of 0.225% and a one week leakage of 52.824%.

EXAMPLE 15

A water phase is prepared by dispersing 5.70 g ChitoClear into 350.00 g water while mixing in a jacketed reactor. The pH of the water phase is then adjusted to 4.7 using concentrated HCl under agitation. The water phase temperature is then increased to 85° C. over 60 minutes and then held at 85° C. fora period of time to hydrolyze the ChitoClear. The water phase temperature is then reduced to 25° C. after the hydrolyzing step over a period of 90 minutes. An oil phase is prepared by mixing 120.00 g perfume oil and 30.00 g isopropyl myristate together along with 3.78 g Mondur MR at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a free oil of 7.358%.

EXAMPLE 16

A water phase is prepared by dispersing 5.70 g ChitoClear into 350.00 g water while mixing in a jacketed reactor. The pH of the water phase is then adjusted to 4.0 using concentrated HCl under agitation. The water phase temperature is then increased to 85° C. over 60 minutes and then held at 85° C. fora period of time to hydrolyze the ChitoClear. The water phase temperature is then reduced to 25° C. after the hydrolyzing step over a period of 90 minutes. An oil phase is prepared by mixing 150.00 g SAS-305 with 3.78 g Mondur MR at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a free oil of 0.006%.

EXAMPLE 17

A water phase is prepared by dispersing 5.70 g ChitoClear into 350.00 g water while mixing in a jacketed reactor. The pH of the water phase is then adjusted to 4.3 using concentrated HCl under agitation. The water phase temperature is then increased to 85° C. over 60 minutes and then held at 85° C. for a period of time to hydrolyze the ChitoClear. The water phase temperature is then reduced to 25° C. after the hydrolyzing step over a period of 90 minutes. An oil phase is prepared by mixing 150.00 g SAS-150 with 3.78 g Mondur MR at room temperature. The oil phase is added to the water phase under high shear milling to obtain an emulsion. The emulsion is heated to 40° C. over 30 minutes and held for 60 minutes. The emulsion is then heated to 85° C. and maintained at this temperature for 6 hours while mixing. The capsules formed at this pH condition had a free oil of 0.005%.

TABLE 2

| Example | Hydrolysis pH | Percent degra- dation 7 days | Percent degra- dation 14 days | Percent degra- dation 21 days | Percent degra- dation 28 days |
|---------|---------------|------------------------------|-------------------------------|-------------------------------|-------------------------------|
| 10 | 6.0 | 2.22 | 5.75 | 8.88 | 11.07 |
| 11 | 3.8 | 29.30 | 57.54 | 68.48 | 73.28 |
| 12 | 4.2 | 24.64 | 52.58 | 62.38 | 67.65 |
| 13 | 4.9 | 28.54 | 52.95 | 61.43 | 64.26 |
| 14 | 4.7 | 21.51 | 44.54 | 54.95 | 60.04 |

Percent degradation is measured according to the OECD Guidelines for the Testing of Chemicals, test method OECD 301B. A copy is available in www.oecd-ilibrary.org.

The shell of the composition according to the invention has a % degradation of at least 40% degradation after 14 days, of at least 50 degradation after at least 20 days, and of at least 60% degradation after at least 28 days when tested according to test method OECD TG 301B.

Articles of Manufacture

When combined with an adjunct material, the combination with the microcapsules can comprise a wide range of novel articles of manufacture. The adjunct material can be one or more of a carrier, a binder, an adhesive, a structurant, a surfactant or deposition aid or adjunct materials described below.

Preferably, the adjunct material is selected from the group consisting of builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing, aids, solvents in addition to said solubilizing agent, a fabric softener active selected from the group consisting of a silicone polymer, a polysaccharide, a clay, a fatty ester, a dispersible polyolefin, a polymer latex and mixtures thereof, pigments, and mixtures thereof, preferably said composition comprises an organic acid, preferably citric acid and/or lactic acid, hydrogenated castor oil, ethoxylated polyethleneimines, preferably PEI 600 EO 20 and/or PEI 600, an enzyme, preferably a cold water amylase, cold water protease and/or xylogluconase.

The microcapsules of the invention can be incorporated dry, as an aqueous slurry, as a coating or as a gel into or onto a variety of commercial products to yield novel and improved articles of manufacture, including incorporation into or onto packaging, dry wall, construction materials, heat sinks for electronics, cooling fluids, incorporated into or onto insulation, used with lotions, incorporated into gels including gels for coating fabrics, automotive interiors, and other structures or articles, including clothing, footwear, personal protective equipment and any other article where use of the improved capsules of the invention is deemed desirable. As used herein, articles of manufacture can be selected from the group consisting of a soap, a surface cleaner, a laundry detergent, a fabric softener, a shampoo, a textile, a paper towel, an adhesive, a wipe, a diaper, a feminine hygiene product, a facial tissue, a pharmaceutical, a napkin, a deodorant, a foam, a pillow, a mattress, bedding, a cushion, a cosmetic, a medical device, an agricultural product, packaging, a cooling fluid, a wallboard and insulation.

The microcapsules protect and separate the core material such as phrase change material, or fragrance or other core material or benefit agent, keeping it separated from the external environment. This facilitates design of distinct and improved articles of manufacture. The microcapsules facilitate improving flowability of encapsulated materials enhancing ease of incorporation into on onto articles such as foams, gels, textiles, various cleaners, detergents or fabric softeners. The microcapsules can be used neat, or more often blended into coatings, gels or used as an aqueous slurry or blended into other articles to form new and improved articles of manufacture. For example, with phase change benefit agents, the microcapsules help preserve the repeated activity of the phase change material and retain the phase change material to prevent leakage or infusion into nearby components when isolation of the microcapsules is desired, yet promote eventual degradation of such encapsulates or portions of the articles of manufacture.

As used herein "cleaning and/or treatment compositions" means products comprising dry or fluid laundry detergents, fabric enhancers, laundry and/or rinse additives, dishwashing detergents, hard surface cleaning and/or treatment compositions, toilet bowl cleaners that may or may not be contained in a unit dose delivery product all for consumer, agricultural, industrial or institutional use.

The term "absorbent article" is used herein in a very broad sense including any article able to receive and/or absorb and/or contain and/or retain fluids and/or exudates, especially bodily fluids/bodily exudates. Exemplary absorbent articles in the context of the present invention are disposable absorbent articles. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable absorbent articles according to the present invention are diapers, surgical and wound dressings, breast and perspiration pads, incontinence pads and pants, bed pads as well as absorbent articles for feminine hygiene like sanitary napkins, panty liners, tampons, interlabial devices or the like. Absorbent articles suitable for use in the present invention include any type of structures, from a single absorbent layer to more complex multi-layer structures. Certain absorbent articles include a fluid pervious topsheet, a backsheet, which may be fluid impervious and/or may be water vapor and/or gas pervious, and an absorbent element comprised there between, often also referred to as "absorbent core" or simply "core".

The term "open cell foam" means a thermoplastic polymer with one or more entrained gases. Typically, open cell foams comprise a polyethylene, polypropylene or other polyalkene polymer. A plurality of microcapsules comprising at least 3%, or even at least 7%, or even up to 30% by weight of the cell foam structure can be usefully employed to form an article of manufacture.

The term "absorbent personal care article" refers to an article with a liquid permeable topsheet, which faces the wearer, and a liquid-impermeable backsheet or outer cover. Disposed between the topsheet and outer cover is an absorbent core. In this regard, the topsheet and outer cover are often joined and/or sealed to encase the absorbent core. Illustrative of such is a disposable diaper. The term can refer other types of personal care articles, including other articles to be worn about or placed adjacent the body. The microcapsules of the present invention at loadings up to about 30% by weight would be useful in absorbent personal care articles. Specific absorbent personal care articles are such as those described in US Patent Publication 20040127866.

The term "sanitary tissue product" or "tissue product" as used herein means a wiping implement for post-urinary and/or post-bowel movement cleaning (toilet tissue products), for otorhinolaryngological discharges (facial tissue products) and/or multi-functional absorbent and cleaning uses (absorbent towels such as paper towel products and/or wipe products). The sanitary tissue products of the present invention may comprise one or more fibrous structures and/or finished fibrous structures, traditionally, but not necessarily, comprising cellulose fibers.

The term "tissue-towel paper product" refers to products comprising paper tissue or paper towel technology in general, including, but not limited to, conventional felt-pressed or conventional wet-pressed tissue paper, pattern densified tissue paper, starch substrates, and high bulk, uncompacted tissue paper. Non-limiting examples of tissue-towel paper products include towels, facial tissue, bath tissue, table napkins, and the like.

"Personal care composition" refers to compositions intended for topical application to skin or hair and can be, for example, in the form of a liquid, semi-liquid cream, lotion, gel, or solid. Examples of personal care compositions can include, but are not limited to, bar soaps, shampoos, conditioning shampoos, body washes, moisturizing body washes, shower gels, skin cleansers, cleansing milks; in-shower body moisturizers, pet shampoos, shaving preparations, etc.

"Bar soap" refers to compositions intended for topical application to a surface such as skin or hair to remove, for example, dirt, oil, and the like. The bar soaps can be rinse-off formulations, in which the product is applied topically to the skin or hair and then subsequently rinsed within minutes from the skin or hair with water. The product could also be wiped off using a substrate. Bar soaps can be in the form of a solid (e.g., non-flowing) bar soap intended for topical application to skin.

"Rinse-off" means the intended product usage includes application to skin and/or hair followed by rinsing and/or wiping the product from the skin and/or hair within a few seconds to minutes of the application step.

"Ambient" refers to surrounding conditions at about one atmosphere of pressure, 50% relative humidity and about 25° C.

"Anhydrous" refers to compositions and/or components which are substantially free of added or free water.

"Antiperspirant composition" refers to antiperspirant compositions, deodorant compositions, and the like. For example, antiperspirant creams, gels, soft solid sticks, body sprays, and aerosols.

"Soft solid" refers to a composition with a static yield stress of about 200 Pa to about 1,300 Pa. The term "solid" includes granular, powder, bar and tablet product forms.

The term "fluid" includes liquid, gel, paste and gas product forms.

The term "situs" includes paper products, fabrics, garments, hard surfaces, hair and skin.

The term "substantially free of" refers to about 2% or less, about 1% or less, or about 0.1% or less of a stated ingredient. "Free of" refers to no detectable amount of the stated ingredient or thing.

As used herein, the terms "a" and "an" mean "at least one".

As used herein, the terms "include", "includes" and "including" are meant to be non-limiting.

Unless specifically stated otherwise, the test methods disclosed in the present application should be used to determine the respective values of the parameters of Applicants' inventions. Similarly, unless otherwise noted, in discussing the commercial applications below, all component or composition levels are in reference to the active portion of that component or composition, and are exclusive of impurities, for example, residual solvents or by-products, which may be present in commercially available sources of such components or compositions.

Similarly, all percentages and ratios are calculated by weight unless otherwise indicated and are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Preferably, said article of manufacture comprises based on total product weight, from 0.001% about to about 25%, preferably from about 0.01% to about 10%, more preferably from about 0.05% to about 5%, most preferably from about 0.1% to about 0.5% of a combination of said microcapsules in or on the article of manufacture.

Additional Article of Manufacture Specifics

Additional product specifics are found below. Such disclosure is also intended to cover the process of making the disclosed products wherein said process comprises combining the microcapsules as disclosed to form the described article of manufacture.

Cleaning and/or Treatment Compositions and Methods of Use

Preferably, said product is a cleaning and/or treatment composition having a viscosity of from about 10 mPa·s to about 50,000 mPa·s, preferably from about 50 mPa·s to about 2000 mPa·s, most preferably from about 75 mPa·s to about 400 mPa·s, a pH from about 3 to about 10, preferably from about 4 to about 8, most preferably from about 5 to about 8, said composition comprising, based on total cleaning and/or treatment composition weight with from 0.001% about to about 25%, preferably from about 0.01% to about 10%, more preferably from about 0.05% to about 5%, most preferably from about 0.1% to about 0.5% of the microcapsules disclosed herein.

As the viscosity range of the cleaning and/or treatment composition is tightened, it is easier to suspend certain materials such as polymers, waxes and microcapsules.

Preferably said cleaning and/or treatment composition comprises:

(a) a surfactant selected from the group consisting of nonionic surfactants, anionic surfactants, cationic surfactants, ampholytic surfactants, zwitterionic surfactants, semipolar nonionic surfactants and mixtures thereof;

(b) a solvent wherein the solvent is preferably selected from the group consisting of hydrogenated castor oil, glycols, alcohols, and mixtures thereof;

(c) a fabric softener active wherein the fabric softener active is preferably selected from the group consisting of a quaternary ammonium compound, an amine and mixtures thereof, preferably said quaternary ammonium compound is selected from the group consisting of bis-(2-hydroxypropyl)-dimethylammonium methylsulphate fatty acid ester, 1,2-di(acyloxy)-3-trimethylammoniopropane chloride, N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate, 1,2 di-(stearoyl-oxy) 3 trimethyl ammoniumpropane chloride, dicanoladimethylammonium chloride, di(hard) tallowdimethylammonium chloride, dicanoladimethyl-ammonium methylsulfate, 1-methyl-1-stearoylamido-ethyl-2-stearoylimidazolinium methylsulfate, 1-tallowylamidoethyl-2-tallowylimidazoline, dipalmethyl hydroxyethylammonium methosulfate and mixtures thereof, and (d) mixtures of (a) through (c).

Additionally, the microcapsules of the invention can be combined to form the following articles of manufacture.

(a) Liquid or powder laundry detergents such as those systems described in U.S. Pat. Nos. 5,929,022 and 5,916,862.

(b) Unit dose pouches, tablets and capsules such as those described in EP 1431382A1, US 2013/0219996 A1, US 2013/0284637 A1, and U.S. Pat. No. 6,492,315. Unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%).

(c) Scent boosters such as those described in U.S. Pat. No. 8,333,289 and US2014/0107010.

(d) Fabric care products such as rinse conditioners (containing 1 to 30 wt % of a fabric conditioning active), fabric liquid conditioners (containing 1 to 30 wt % of a fabric conditioning active), tumble drier sheets, fabric refreshers, fabric refresher sprays, ironing liquids, and fabric softener systems such as those described in U.S. Pat. Nos. 6,335,315 and 5,877,145.

(e) Liquid fabric softeners/fresheners containing benefit agent-containing microcapsules according to the invention and at least one fabric softening agent present, preferably, at a concentration of 1 to 30% (e.g., 4 to 20%, 4 to 10%, and 8 to 15%). The ratio between the benefit agent and the fabric softening agent can be 1:500 to 1:2 (e.g., 1:250 to 1:4 and 1:100 to 1:8). As an illustration, when the fabric softening agent is 5% by weight of the fabric softener, the benefit agent is 0.01 to 2.5%, preferably 0.02 to 1.25% and more preferably 0.1 to 0.63%. As another example, when the fabric softening agent is 20% by weight of the fabric softener, the benefit agent is 0.04 to 10%, preferably 0.08 to 5% and more preferably 0.4 to 2.5%. The benefit agent is a fragrance, malodor counteractant or mixture thereof. The liquid fabric softener can have 0.15 to 25% of microcapsules.

(f) Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390.

Up to about 30% by weight of microcapsules according to the invention can be combined into on onto liquid dish detergents such as those described in U.S. Pat. Nos. 6,069, 122 and 5,990,065; automatic dish detergents such as those described in U.S. Pat. Nos. 6,020,294 and 6,017,871; all-purpose cleaners including bucket dilutable cleaners and toilet cleaners; bathroom cleaners; bath tissue; rug deodorizers; candles; room deodorizers; floor cleaners; disinfectants; window cleaners; garbage bags and trash can liners; air fresheners including room deodorizer and car deodorizer, scented candles, sprays, scented oil air freshener, automatic spray air freshener, and neutralizing gel beads; moisture absorbers; household devices such as paper towels and disposable wipes; moth balls, traps and cakes; insect attractants and repellants; baby care products such as diaper rash cream and balm, diapers, and bibs; and feminine hygiene products such as tampons, feminine napkins and wipes, and pantiliners.

Up to about 30% by weight of microcapsules according to the invention can also be combined into on onto personal care products, such as cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically, these products can include personal cleansers (bar soaps, body washes, and shower gels); in-shower conditioner; sunscreen and tattoo color protection (sprays, lotions, and sticks); insect repellants; hand sanitizer; anti-inflammatory balms, ointments, and sprays; antibacterial ointments and creams; sensates; deodorants and antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant; wax based deodorant, an example of the formulation being paraffin wax (10-20%), hydrocarbon wax (5-10%), white petrolatum (10-15%), acetylated lanolin alcohol (2-4%), diisopropyl adipate (4-8%), mineral oil (40-60%) and preservative (as needed), and prepared by (i) mixing the ingredients of the formulation, (ii) heating the resultant composition to 75° C. until melted, (iii) with stirring, adding 4% cryogenically ground polymer containing a fragrance while maintaining the temperature at 75° C., and (iv) stirring the resulting mixture in order to ensure a uniform suspension while a microcapsules of this invention are added to the formulation; glycol/soap type deodorant, an example of the formulation being propylene glycol (60-70%), sodium stearate (5-10%), distilled water (20-30%), 4.2,4,4-Trichloro-2'-Hydroxy Diphenyl Ether, manufactured and trademarked by the Ciba-Geigy Chemical Company (0.01-0.5%), and prepared by (i) combining the ingredients of the formulation, (ii) heating to 75° C. with stirring until the sodium stearate has dissolved, cooling the resulting mixture to 40° C., and (iii) adding microcapsules of this invention; lotion including body lotion, facial lotion, and hand lotion; body powder and foot powder; toiletries; body spray; shave cream and male grooming products; bath soak; and exfoliating scrub.

Up to about 30% by weight of microcapsules according to the invention can also be combined into on onto personal care devices such as facial tissues and cleansing wipes; hair care products such as liquid and dry powder shampoos, hair conditioners (rinse-out, leave-in and cleansing), hair rinses, hair refreshers, hair perfumes, hair straightening products, hair styling products, hair fixatives, hair styling aids, hair combing creams, hair wax, hair foam, hair gel, nonaerosol pump spray, hair bleaches, hair dyes, hair colorants, perming agents and hair wipes; alcohol based fine fragrance, with compositions and methods for incorporating fragrance capsules as described in U.S. Pat. No. 4,428,869 and an example of the formulation being ethanol (1-99%) and water (0-99%), a suspending aide [including but not limited to: hydroxypropyl cellulose, ethyl cellulose, silica, microcrystalline cellulose, carrageenan, propylene glycol alginate, methyl cellulose, sodium carboxymethyl cellulose or xanthan gum] (0.-1-%) and optionally an emulsifier or an emollient [including but not limited to those listed above]; solid perfume; lipstick and lip balm; make-up cleanser; skin care cosmetics such as foundation, pack, sunscreen, skin lotion, milky lotion, skin cream, emollients, and skin whitening; make-up cosmetics such as manicure products, mascara, eyeliner, eye shadow, liquid foundation, powder foundation, and cheek rouge; consumer goods packaging such as fragranced cartons, and fragranced plastic bottles and boxes; pet care products such as cat litter, flea and tick treatment products; pet grooming products, pet shampoos, pet toys, pet treats, chewables, pet training pads, and pet carriers and crates In one aspect of Applicants' cleaning and/or treatment composition, said cleaning and/or treatment composition comprises a fabric softener active selected from the group consisting of a quaternary ammonium compound, a silicone polymer, a polysaccharide, a clay, an amine, a fatty ester, a dispersible polyolefin, a polymer latex and mixtures thereof, preferably (a) said quaternary ammonium compound comprises an alkyl quaternary ammonium compound, preferably said alkyl quaternary ammonium compound is selected from the group consisting of a monoalkyl quaternary ammonium compound, a dialkyl quaternary ammonium compound, a trialkyl quaternary ammonium compound and mixtures thereof;

(b) said silicone polymer is selected from the group consisting of cyclic silicones, polydimethylsiloxanes, aminosilicones, cationic silicones, silicone polyethers, silicone resins, silicone urethanes, and mixtures thereof;

(c) said polysaccharide comprises a cationic starch;

(d) said clay comprises a smectite clay;

(e) said dispersible polyolefin is selected from the group consisting of polyethylene, polypropylene and mixtures thereof; and (f) said fatty ester is selected from the group consisting of a polyglycerol ester, a sucrose ester, a glycerol ester and mixtures thereof.

In one aspect of Applicants' cleaning and/or treatment composition, said cleaning and/or treatment composition comprises a fabric softener active comprising a material selected from the group consisting of monoesterquats, diesterquats, triesterquats, and mixtures thereof, preferably, said monoesterquats and diesterquats are selected from the group consisting of bis-(2-hydroxypropyl)-dimethylammonium methylsulfate fatty acid ester and isomers of bis-(2-hydroxypropyl)-dimethylammonium methylsulfate fatty acid ester and/or mixtures thereof, 1,2-di(acyloxy)-3-trimethylammoniopropane chloride, N,N-bis(stearoyl-oxyethyl)-N,N-dimethyl ammonium chloride, N,N-bis(tallowoyl-oxy-ethyl)-N,N-dimethyl ammonium chloride, N,N-bis(stearoyl-oxy-ethyl)-N-(2-hydroxyethyl)-N-methyl ammonium methylsulfate, N,N-bis-(stearoyl-2-hydroxypropyl)-N,N-dimethylammonium methylsulfate, N,N-bis-(tallowoyl-2-hydroxypropyl)-N,N-dimethylammonium methylsulfate, N,N-bis-(palmitoyl-2-hydroxypropyl)-N,N-dimethylammonium methylsulfate, N,N-bis-(stearoyl-2-hydroxypropyl)-N,N-dimethylammonium chloride, 1,2-di-(stearoyl-oxy)-3-trimethyl ammoniumpropane chloride, dicanoladimethyl-ammonium chloride, di(hard)tallowdimethylammonium chloride, dicanoladimethylammonium methylsulfate, 1-methyl-1-stearoylamidoethyl-2-stearoylimidazolinium methylsulfate, 1-tallowylamidoethyl-2-tallowylimidazoline, dipalmylmethyl hydroxyethylammonium methylsulfate and mixtures thereof.

In one aspect of Applicants' cleaning and/or treatment composition, said composition comprises a quaternary ammonium compound and a silicone polymer, preferably said composition comprises from 0.001% to 10%, from 0.1% to 8%, more preferably from 0.5% to 5%, of said silicone polymer.

In one aspect of Applicants' cleaning and/or treatment composition, said fabric softening active has an Iodine Value of between 0-140, preferably 5-100, more preferably 10-80, even more preferably, 15-70, most preferably 18-25 or when said fabric softening active comprises a partially hydrogenated fatty acid quaternary ammonium compound said fabric softening active most preferably has an Iodine Value of 25-60.

In one aspect of Applicants' cleaning and/or treatment composition, said cleaning and/or treatment composition is a soluble unit-dose product said soluble unit dose product comprising one or more cleaning and/or treatment compositions contained within one or more chambers said chambers being formed from one or more films, preferably said one or more films comprise PVA film.

The compositions of the present invention may be used in any conventional manner. In short, they may be used in the same manner as products that are designed and produced by conventional methods and processes. For example, compositions of the present invention can be used to treat a situs inter alia a surface or fabric. Typically, at least a portion of the situs is contacted with an aspect of Applicants' composition, in neat form or diluted in a wash liquor, and then the situs is optionally washed and/or rinsed. For purposes of the present invention, washing includes but is not limited to, scrubbing, and mechanical agitation. The fabric may comprise any fabric capable of being laundered in normal consumer use conditions. When the wash solvent is water, the water temperature typically ranges from about 5° C. to about 90° C. and, when the situs comprises a fabric, the water to fabric mass ratio is typically from about 1:1 to about 100:1.

The cleaning and/or treatment compositions of the present invention may be used as liquid fabric enhancers wherein they are applied to a fabric and the fabric is then dried via line drying and/or drying in an automatic dryer.

In one aspect, a method of controlling malodors comprising: contacting a situs comprising a malodor and/or a situs that will become malodorous with a cleaning and/or treatment composition selected from the group consisting of Applicants' cleaning and/or treatment compositions and mixtures thereof, is disclosed.

In one aspect of Applicants' method, said situs comprises a fabric and said contacting step comprises contacting said fabric with a sufficient amount of Applicants' cleaning and/or treatment compositions to provide said fabric with at least 0.0025 mg of benefit agent, such as perfume, per kg of fabric, preferably from about 0.0025 mg of benefit agent/kg of fabric to about 50 mg of malodor reduction material/kg of fabric, more preferably from about 0.25 mg of benefit agent/kg of fabric to about 25 mg of benefit agent/kg of fabric, most preferably from about 0.5 of benefit agent/kg of fabric to about 10 mg of benefit agent/kg of fabric of said sum of malodor reduction materials.

Solid Articles of Manufacture and Methods of Use

The article of manufacture can be a product which is a powder, granule, flake, bar or bead, said product comprising, based on total product weight:

(a) from 0.001% to about 25% or even up to 30%, preferably from about 0.01% to about 10%, more preferably from about 0.05% to about 5%, most preferably from about 0.1% to about 0.5% by weight of the microcapsules disclosed herein;

(b) a carrier that is a solid at 25° C., preferably said solid carrier is selected from the group consisting of clays, sugars, salts, silicates, zeolites, citric acid, maleic acid, succinic acid, benzoic acid, urea and polyethylene oxide and mixtures thereof; preferably said carriers is present at a level of:
  (i) from about 20% to about 95%, more preferably about 30% to about 90%, even more preferably about 45% to about 90%, and most preferably about 60% to about 88%; or
  (ii) from about 1% to about 60%, more preferably about 2% to about 50%, even more preferably about 3% to about 45% and most preferably, about 4% to about 40%; and (c) optionally, 0.5% to about 50% of an enzyme stable polymer, preferably said enzyme stable polymer is selected from the group consisting of polyacrylate polymers, polyamine polymer, acrylate/maleate copolymer, a polysaccharide, and mixtures thereof, preferably said polysaccharide is selected from the group consisting of carboxy methyl cellulose, cationic hydroxy ethyl cellulose and mixtures thereof.

In one aspect of said article of manufacture, said article comprises a perfume.

In one aspect of said article of manufacture, said article comprises an additional material that is an adjunct ingredient selected from the group consisting of surfactants, builders, chelating agents, dye transfer inhibiting agents, dispersants, enzymes, and enzyme stabilizers, catalytic materials, bleach activators, a fabric softener active, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing aids, solvents, pigments and mixtures thereof.

The compositions of the present invention may be used in any conventional manner. For example, compositions of the present invention can be used to treat a situs inter alia a surface or fabric. Typically, at least a portion of the situs is contacted with an aspect of Applicants' composition of added microcapsules, in neat form or diluted in a wash liquor, and then the situs is optionally washed and/or rinsed.

For purposes of the present invention, washing includes but is not limited to, scrubbing, and mechanical agitation. The fabric may comprise any fabric capable of being laundered in normal consumer use conditions. When the wash solvent is water, the water temperature typically ranges from about 5° C. to about 90° C. and, when the situs comprises a fabric, the water to fabric mass ratio is typically from about 1:1 to about 100:1.

The compositions of the present invention may be used as fabric enhancers wherein they are applied to a fabric and the fabric is then dried via line drying and/or drying in an automatic dryer.

A method of freshening comprising contacting a situs comprising with a product selected from the group consisting of the products described herein and mixtures thereof, is disclosed.

Freshening Compositions, Methods of Use and Delivery Systems

Preferably, said article of manufacture is a freshening composition having a viscosity of from about 1 mPa·s to about 50,000 mPa·s, preferably from about 1 mPa·s to about 2000 mPa·s, most preferably from about 1 mPa·s to about 400 mPa·s, a pH from about 3 to about 10, preferably from about 4 to about 8, most preferably from about 5 to about 8, said freshening composition comprising, based on total freshening composition weight:

(a) with from 0.001% about to about 25%, preferably from about 0.01% to about 10%, more preferably from about 0.05% to about 5%, most preferably from about 0.1% to about 0.5% of the microcapsules disclosed here in; and (b) from about 0.01% to about 3%, preferably from about 0.4% to about 1%, more preferably from about 0.1% to about 0.5%, most preferably from about 0.1% to about 0.3% of solubilizing agent, preferably said solubilizing agent is selected from the group consisting of a surfactant, a solvent and mixtures thereof,
  (i) preferably said surfactant comprises a non-ionic surfactant;
  (ii) preferably said solvent comprises an alcohol, a polyol and mixtures thereof;

(c) optionally, an adjunct ingredient.

As the viscosity is lowered you obtain improved sprayability and improved penetration into fabric.

In one aspect of said freshening composition, said composition comprises an adjunct ingredient selected from the group consisting of isoalkanes comprising at least 12 carbon atoms, a compound comprising a quaternary amine moiety, lubricants, additional solvents, glycols, alcohols, silicones, preservatives, anti-microbial agents, pH modifiers, a carrier, insect repellants, metallic salts, cyclodextrins, functional polymers, anti-foaming agents, antioxidants, oxidizing agents, chelants and mixtures thereof; preferably lubricants wherein the lubricants preferably comprise hydrocarbons, more preferably hydrocarbons that comprise two or more branches or compounds comprising a quaternary amine moiety comprising at least 10 carbon atoms.

A device comprising Applicants' freshening compositions, said device being preferably selected from the group consisting of trigger sprayers, manual aerosol sprayers, automatic aerosol sprayers, wick containing devices, fan devices, and thermal drop-on-demand devices, is disclosed.

A method of freshening comprising contacting a situs with a composition selected from the group consisting of the freshening compositions disclosed herein and mixtures thereof is disclosed.

In one aspect of said method, said contacting step comprises contacting said situs with a sufficient amount of the compositions disclosed herein to provide said situs with, from about 0.1 milligrams (mg) to about 10,000 mg, preferably from about 1 mg to about 5,000 mg most preferably from about 5 mg to about 1000 mg of a benefit agent, preferably a perfume, per square meter of projected surface area of said situs.

The composition of the present invention may be used with a hard surface cleaner, as is commonly used to clean countertops, tables and floors. The cleaning solution may particularly be made according to the teachings of U.S. Pat. No. 6,814,088. The reservoir may be used with and dispensed from a floor cleaning implement, in conjunction with a disposable floor sheet. A suitable reservoir and fitment therefore may be made according to the teachings of U.S. Pat. Nos. 6,386,392 and/or 7,172,099. If desired the floor cleaning implement may dispense steam, according to the teachings of US 2013/0319463. Alternatively, a refillable reservoir may be utilized.

If desired the composition of the present invention may be used with a pre-moistened sheet. If the cleaning sheet is pre-moistened, it is preferably pre-moistened with a liquid which provides for cleaning of the target surface, such as a floor, but yet does not require a post-cleaning rinsing operation. The cleaning sheet may be loaded with at least 1, 1.5 or 2 grams of cleaning solution per gram of dry substrate, but typically not more than 5 grams per gram. The cleaning solution may comprise a surfactant, such as APG surfactant which minimizes streaking since there is typically not a rinsing operation, according to the teachings of U.S. Pat. No. 6,716,805.

The composition of the present invention may be used for hard surface cleaners or polishers. The composition may be dispensed from a trigger sprayer or aerosol sprayer, as are well known in the art. An aerosol sprayer dispenses the composition using propellant pressure, while a trigger sprayer dispenses the composition by pumping the composition under manual actuation. A suitable aerosol dispenser may have a dip tube or bag on valve, according to US 2015/0108163 and/or US 2011/0303766. A suitable trigger sprayer is found in U.S. Pat. No. 8,322,631.

The present freshening composition may be used in a device for the delivery of a volatile material to the atmosphere or on inanimate surfaces (e.g. fabric surfaces as a fabric refresher). Such device may be configured in a variety of ways. For example, the device may be configured for use as an energized air freshener (i.e. powered by electricity; or chemical reactions, such as catalyst fuel systems; or solar powered; or the like). Exemplary energized air freshening devices include a powered delivery assistance means which may include a heating element, fan assembly, or the like. More particularly, the device may be an electrical wall-plug air freshener as described in U.S. Pat. No. 7,223,361; a battery (including rechargeable battery) powered air freshener having a heating and/or fan element. In energized devices, the volatile material delivery engine may be placed next to the powered delivery assistance means to diffuse the volatile perfume material. The volatile perfume material may be formulated to optimally diffuse with the delivery assistance means.

Alternatively, the device may be configured for use as a non-energized air freshener. An exemplary non-energized air freshener includes a reservoir and, optionally, capillary or wicking means or an emanating surface, to help volatile materials passively diffuse into the air (i.e. without an energized means). A more specific example includes a delivery engine having a liquid reservoir for containing a volatile material and a microporous membrane enclosing the liquid reservoir as disclosed in U.S. Pat. Nos. 8,709,337 and 8,931,711.

The device may also be configured for use as an aerosol sprayer or a nonaerosol air sprayer including traditional trigger sprayers as well as trigger sprayer having a pre-compression and/or buffer system for fluid therein. In this embodiment, the delivery engine can deliver volatile materials upon user demand or programmed to automatically deliver volatile materials to the atmosphere.

The apparatus may also be configured for use with an air purifying system to deliver both purified air and volatile materials to the atmosphere. Non-limiting examples include air purifying systems using ionization and/or filtration technology for use in small spaces (e.g. bedrooms, bathrooms, automobiles, etc.), and whole house central air conditioning/heating systems (e.g. HVAC).

Article and Method of Use

Preferably said article of manufacture comprises (a) a substrate, preferably a flexible substrate, more preferably a flexible substrate that is a sheet; preferably said substrate comprises a fabric softening active, preferably said fabric softening active coats all or a portion of said substrate; and (b) based on total article weight with from 0.001% about to about 25%, or even up to 30%, preferably from about 0.01% to about 10%, more preferably from about 0.05% to about 5%, most preferably from about 0.1% to about 0.5% of the microcapsules disclosed herein.

Preferably said article has a weight ratio of fabric softener active to dry substrate ranging from about 10:1 to about 0.5:1, preferably from about 5:1 to about 1:1, preferably said fabric softener active is selected from the group consisting of a quaternary ammonium compound, a silicone polymer, a polysaccharide, a clay, an amine, a fatty ester, a dispersible polyolefin, a polymer latex and mixtures thereof.

In one aspect, said article has a weight ratio of fabric softener active to dry substrate ranging from about 10:1 to about 0.5:1, preferably from about 5:1 to about 1:1, preferably said fabric softener active is selected from the group consisting of (a) a cationic fabric softener active, preferably a quaternary-ammonium fabric softener active, more preferably a di(long alkyl chain)dimethylammonium (C1-C4 alkyl) sulfate or chloride, preferably the methyl sulfate; an ester quaternary ammonium compound, an ester amine precursor of an ester quaternary ammonium compound, and mixtures thereof, preferably a diester quaternary ammonium salt;

(b) a carboxylic acid salt of a tertiary amine and/or ester amine;

(c) a nonionic fabric softener material, preferably fatty acid partial esters of polyhydric alcohols, or anhydrides thereof, wherein the alcohol or anhydride contains from about 2 to about 18 and preferably from about 2 to about 8 carbon atoms, and each fatty acid moiety contains from about 8 to about 30 and preferably from about 12 to about 20 carbon atoms;

(d) alkanolamides;

(e) fatty acids; and (f) mixtures of the foregoing.

Preferably, said article comprises, based on total article weight, from 1% to 99% by weight, preferably from about 1% to about 80%, more preferably from about 20% to about 70%, most preferably from about 25% to about 60% of a fabric softening active.

Preferably said article comprises a quaternary ammonium compound selected from the group consisting of bis-(2-hydroxypropyl)-dimethylammonium methylsulphate fatty acid ester, 1,2-di(acyloxy)-3-trimethylammoniopropane chloride, N, N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate, 1,2 di (stearoyl-oxy) 3 trimethyl ammoniumpropane chloride, dicanoladimethylammonium chloride, di(hard)tallowdimethylammonium chloride, dicanoladimethylammonium methylsulfate, 1-methyl-1-stearoylamidoethyl-2-stearoylimidazolinium methylsulfate, 1-tallowylamidoethyl-2-tallowylimidazoline, dipalmethyl hydroxyethylammonium methosulfate and mixtures thereof.

In one aspect of said article, said article comprises a fabric softening active having an Iodine Value of between 0-140, preferably 5-100, more preferably 10-80, even more preferably, 15-70, most preferably 18-25.

In one aspect of said article, said article comprises an adjunct ingredient selected from the group consisting of surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing aids, solvents, pigments anti-oxidants, colorants, preservatives, optical brighteners, opacifiers, stabilizers such as guar gum and polyethylene glycol, anti-shrinkage agents, anti-wrinkle agents, soil release agents, fabric crisping agents, reductive agents, spotting agents, germicides, fungicides, anti-corrosion agents, antifoam agents, color care agents including chlorine scavengers, dye transfer inhibitors, dye fixatives, chelants, anti-abrasion agents, perfume, perfume microcapsules, cyclodextrin perfume complexes, free cyclodextrin, pro-perfumes; antioxidants and mixtures thereof.

A method of controlling softening and/or freshening comprising contacting a situs comprising one or more of the articles Applicants' disclose herein, is disclosed.

In one aspect of said method, said situs comprises a fabric and said contacting step comprises contacting said fabric with a sufficient amount of Applicants' article containing to provide said fabric with a level of perfume of at least 0.0025 mg of perfume/kg of fabric, preferably from about 0.00025 mg of perfume/kg of fabric to about 25 mg of perfume/kg of fabric, more preferably from about 0.025 mg of perfume/kg of fabric to about 20 mg of perfume/kg of fabric, most preferably from about 0.25 of perfume/kg of fabric to about 10 mg of malodor reduction material/kg of fabric of said sum of malodor reduction materials.

One aspect of the present invention relates to fabric conditioning compositions which are delivered to fabric via dryer-added substrate that effectively releases the composition in an automatic laundry (clothes) dryer. Such dispensing means can be designed for single usage or for multiple uses. The dispensing means can also be a "carrier material" that releases the fabric conditioning composition and then is dispersed and/or exhausted from the dryer. When the dispensing means is a flexible substrate, e.g., in sheet configuration, the fabric conditioning composition is releasably affixed on the substrate to provide a weight ratio of conditioning composition to dry substrate ranging from about 10:1 to about 0.5:1, preferably from about 5:1 to about 1:1. To insure release, preferred flexible sheets withstand the dryer environment without decomposing or changing shape, e.g. combusting, creating off odors, or shrinking with heat or moisture. Substrates especially useful herein are rayon and/or polyester non-woven fabrics.

Non-limiting examples of the substrates useful herein are cellulosic rayon and/or polyester non-woven fabrics having basis weights of from about 0.4 oz./yd$^2$ to about 1 oz./yd$^2$, preferably from about 0.5 oz./yd$^2$ to about 0.8 oz./yd$^2$, more preferably from about 0.5 oz./yd$^2$ to about 0.6 oz./yd$^2$. These substrates are typically prepared using, e.g., rayon and/or polyester fibers having deniers of from about 1 to about 8, preferably from about 3 to about 6, and more preferably about 4 to 6 or mixtures of different deniers. Typically, the fiber is a continuous filament or a $\frac{3}{16}$ inch to 2 inch fiber segment that is laid down, in a pattern that results in a multiplicity of layers and intersections between overlaid portions of the filament or fiber, on a belt, preferably foraminous, and then the fiber intersections are glued and/or fused into fiber-to-fiber bonds by a combination of an adhesive binder, and/or heat and/or pressure. As non-limiting examples, the substrate may be spun-bonded, melt-bonded, or point bonded or combinations of bonding processes may be chosen. The substrate breaking strength and elasticity in the machine and cross direction is sufficient to enable the substrate to be conveyed through a coating process. The porosity of the substrate article is sufficient to enable air flow through the substrate to promote conditioning active release and prevent dryer vent blinding. The substrate may also have a plurality of rectilinear slits extended along one dimension of the substrate.

The dispensing means will normally carry an effective amount of fabric conditioning composition. Such effective amount typically provides sufficient softness, antistatic effect and/or perfume deposition for at least one treatment of a minimum load in an automatic laundry dryer. Amounts of the fabric conditioning composition irrespective of load size for a single article can vary from about 0.1 g to about 100 g, preferably from about 0.1 g to about 20 g, most preferably from about 0.1 g to about 10 g. Amounts of fabric treatment composition for multiple uses, e.g., up to about 30, can be used.

Absorbent Article, Polybag or Paper Carton and Methods of Use

Preferably said article of manufacture is an article selected from an absorbent article, polybag or paper carton, said article comprising, based on total article weight, with from 0.001% about to about 25%, preferably from about 0.01% to about 10%, more preferably from about 0.05% to about 5%, most preferably from about 0.1% to about 0.5% of the microcapsules of the present invention.

Preferably said article is an absorbent article, preferably said absorbent article is a sanitary paper product, said sanitary paper product comprising one or more layers of conventional felt-pressed tissue paper, conventional wet-pressed tissue paper, pattern densified tissue paper, starch substrates, high bulk, un-compacted tissue paper and mixtures thereof.

Preferably said absorbent article comprises an absorbent core, and optionally a backsheet, topsheet, acquisition layer or outer wrapper, wherein said microcapsules are disposed on the absorbent core or between one or more of the optional layers.

In one aspect of said article, said absorbent article is contained in a polybag or paper carton.

In one aspect of said article, said microcapsules are disposed on said polybag or paper carton, and/or on said absorbent article.

Preferably said article is an absorbent article that comprises a lotion.

Preferably, said absorbent article comprises one or more adjunct ingredients selected from the group consisting of surfactants, inks, dyes, mineral oils, petrolatum, polysiloxanes, cyclodextrins, clays, silicates, aluminates, vitamins, isoflavones, flavones, metal oxides, short chain organic acids ($C_1$-$C_8$), triglycerides ($C_8$-$C_{22}$), and antioxidants.

In one aspect, a method of providing a benefit agent, preferably perfume, comprising incorporating said microcapsules in or on an article, preferably an absorbent article, polybag and/or paper carton, is disclosed.

A non-limiting list of suppliers of suitable absorbent articles, polybags, and cartons that can be used in the manufacture of Applicants' articles is disclosed in U.S. Pat. No. 10,308,894, Feng et al. Suitable equipment and processes for making absorbent articles can be obtained from Fameccanica Group of Pescara, Italy. Suitable equipment and processes for adding the malodor reduction materials to said articles can be obtained from Nordson of Duluth Ga., USA.

Article of Manufacture—Latex Foam Bedding

The microcapsules of the invention can be used in or on latex foam bedding products with, for example, phase change microcapsules (PCM) incorporated into latex foam. The microcapsules may be used for many bedding product applications but are particularly suitable for use in or on latex foam mattresses and pillows.

A bedding product is preferably a mattress. A bedding product can include a first layer comprised of latex foam including a plurality of microcapsules distributed on or throughout the foam. The bedding product further includes one or more additional layers adjacent the first layer of latex foam and/or poly materials.

The thickness of the first layer is generally determined by comfort level, however, with regards to temperature regulation, as the foam thickness increases so does the absolute amount of PCM. A first layer may have a thickness ranging from about 0.4 inches up to about 6 inches. The preferred thickness has been found to be in the range of about 0.75 inches to about 3 inches for temperature regulating impact and comfort. A portion of the first layer can include microcapsules. The microcapsules have an outer shell and include, inside the shell, a phase change material, such as a wax, that absorbs and releases energy by changing phase.

In an alternative article of manufacture design, a mattress, for example, can include an upper layer finishing fabric and a functional layer containing fragrance microcapsules between such upper layer and a lower layer. Movement of the user results in fracture of fragrance microcapsules providing a burst of fragrance or gradual emission of fragrance. In a further embodiment, fragrance microcapsules and phase change microcapsules can be used in combination in the article of manufacture, with the latter being of thicker or stronger shell resistant to fracture.

The microcapsules of the invention may be mixed with an effective amount of a fabric conditioning composition and coated onto a dispensing means to form a tumble drier article. Such articles both condition fabrics in a tumble drier and impart a pleasant fragrance. The fabric conditioning composition has a preferred melting (or softening) point of 35° C. to 150° C.

In one embodiment the microcapsules are mixed with a fabric conditioning composition, preferably 1% to 20%, or even 30% microcapsules are mixed with the conditioning composition and most preferably 2% to 10% microcapsules are mixed with the conditioning composition. Because the fragrance is incorporated into the microcapsules, fragrance loss during manufacturing, storage and use is significantly reduced over sheets containing fragrance incorporated by conventional means.

The fabric conditioning composition which may be employed in the invention is coated onto a dispensing means which effectively releases the fabric conditioning composition in a tumble dryer. Such dispensing means can be designed for single usage or for multiple use. One such multi-use article comprises a sponge material releasably enclosing enough of the conditioning composition to impart effective fabric softening during several drying cycles. This multi-use article can be made by filling a porous sponge with the composition. In use, the composition melts and leaches out through the pores of the sponge to soften and condition fabrics.

Another article comprises a cloth or paper bag releasably enclosing the composition and sealed with a hardened plug of the mixture. The action and heat of the dryer opens the bag and releases the composition to perform its softening.

A preferred article comprises the compositions containing a softener and a compatible organosilicone releasably affixed to a flexible substrate such as a sheet of paper or woven or non-woven cloth substrate. When such an article is placed in an automatic laundry dryer, the heat, moisture and tumbling action of the dryer removes the composition from the substrate and deposits it on the fabrics.

The substrates used in the article can have a dense, or more preferably, open or porous structure. Examples of suitable materials which can be used as substrates herein include paper, woven cloth, and non-woven cloth. The term "cloth" herein means a woven or non-woven substrate for the articles of manufacture, as distinguished from the term "fabric" which encompasses the clothing fabrics being dried in an automatic dryer.

Most substances are able to absorb a liquid substance to some degree; however, the term "absorbent", as used herein, is intended to mean a substrate with an absorbent capacity (i.e., a parameter representing a substrate's ability to take up and retain a liquid) from 4 to 12, preferably 5 to 7 times its weight of water.

If the substrate is a foamed plastics material, the absorbent capacity is preferably in the range of 15 to 22, but some special foams can have an absorbent capacity in the range from 4 to 12.

Extrudate Article of Manufacture

Articles of manufacture can be formed with microcapsules of the invention by blending in similar amounts or proportions to those mentioned in discussion of other articles of manufacture herein, a plurality of capsules, such as capsules with lubricating oils in combination with a carrier polymeric resin.

Such combinations can be dry-blended or melt-blended combinations, and enable formation of components for use in sliding applications or applications with rubbing contacts between surfaces such as a piston for automotive engines, conveyer belts, seal assembly for turbines, seal assembly for compressors, sealing elements and the like, comprising a self-lubricating polymeric composition formed by blending a plurality of microcapsules with at least a carrier polymeric resin, and optional subsequent melt-blending with a polymeric matrix.

The amount of microcapsules can range from 1% to 80% by weight, or from 1% to 30%, or even more typically from 10% to 50% by weight.

Examples of carrier polymers having a low melting point include but not limited to polyesters such as polyethylene terephthalate, polybutylene terephthalate; polycarbonate including polycarbonate homopolymers, polyestercarbonate copolymers, linear aromatic polycarbonate resins, branched aromatic polycarbonate resins and poly(ester-carbonate) resins; polyamides such as nylon 6, nylon 66, nylon 12, polyacetal, polyolefins such as polyethylene or polypropylene, copolymers (including terpolymers, etc.) of olefins, halogenated vinyl or vinylidene polymers such as polyvinyl chloride, polyvinylidene chloride, polyvinyl fluoride, polyvinylidene fluoride and copolymers of these monomers with each other or with other unsaturated monomers, polyamide copolymers, styrene polymers and copolymers, polyacrylonitrile, thermoplastic silicone resins, thermoplastic polyethers, polyketones, polyimides, thermoplastic modified celluloses, polysulphones and mixtures thereof.

In embodiments wherein the microcapsules are dry-blended into a carrier polymer forming a dry blend mixture, the carrier polymer may be the same or different from the polymer comprising the base polymer matrix, i.e., a high-temperature thermoplastic resin or a polymeric resin with a melting point <285° C. as listed above.

Examples of high-temperature polymers for use as the carrier polymer of the microcapsules include semi-crystalline as well as amorphous polymers. Examples of high-temperature semi-crystalline polymers include polyarylene sulfide such as polyphenylene sulfide (PPS), polyetheretherketone (PEEK), polyetherketone (PEK), polyphthalamide (PPA), polyetherketoneketone (PEKK), thermoplastic polyimide (TPI), high temperature nylon (HTN), and blends thereof. Examples of high-temperature amorphous polymers include polysulfone (PSU), polyethersulfone (PES), polyetherimide (PEI), and blends thereof.

In certain embodiments, polyethylene terephthalate is used as a carrier for the microcapsules for a composition with polyetherimide as the base polymer. Alternatively, polyethylene terephthalate is used as a carrier for a composition comprising polyetherether ketone, or polycarbonate is used as a carrier for a self-lubricating polyetherether ketone composite, or polyamide is used as a carrier for a polyetherether ketone composition.

The amount of carrier polymer ranges from 5 to about 40 wt %, based upon the total weight of the final composition. In a second embodiment, the amount of carrier polymer ranges from 5 to 30 wt % based on the total weight of the composition. In a third embodiment, the amount of carrier polymer ranges from 5 to 20 wt % based on the total weight of the composition.

The matrix polymeric material can include any polymer (or mixture of polymers) that has or provides one or more desired physical properties for a polymeric composite or an article made therefrom. Examples of physical properties include mechanical properties (e.g., ductility, tensile strength, and hardness), thermal properties (e.g., thermo-formability), and chemical properties (e.g., reactivity).

The matrix polymeric material can be compatible or miscible with or have an affinity for the carrier polymer. Such affinity can depend on, for example, similarity of solubility parameters, polarities, hydrophobic characteristics, or hydrophilic characteristics of the carrier polymeric material and the matrix polymeric material.

Examples of the matrix polymer include but are not limited to polyamides (e.g., Nylon 6, Nylon 6/6, Nylon 12, polyaspartic acid, polyglutamic acid, and so forth), polyamines, polyimides, polyacrylics (e.g., polyacrylamide, polyacrylonitrile, esters of methacrylic acid and acrylic acid, and so forth), polycarbonates (e.g., polybisphenol A carbonate, polypropylene carbonate, etc.), polydienes (e.g., polybutadiene, polyisoprene, polynorbornene, etc.), polyepoxides, polyesters (e.g., polyethylene terephthalate, polybutylene terephthalate, polytrimethylene terephthalate, polycaprolactone, polyglycolide, polylactide, polyhydroxybutyrate, polyhydroxyvalerate, polyethylene adipate, polybutylene adipate, polypropylene succinate, etc.), polyethers (e.g., polyethylene glycol (polyethylene oxide), polybutylene glycol, polypropylene oxide, polyoxymethylene (paraformaldehyde), polytetramethylene ether (polytetrahydrofuran), polyepichlorohydrin, etc.), polyflourocarbons, formaldehyde polymers (e.g., urea-formaldehyde, melamine-formaldehyde, phenol formaldehyde, etc.), natural polymers (e.g., cellulosics, chitosans, lignins, waxes, etc.), polyolefins (e.g., polyethylene, polypropylene, polybutylene, polybutene, polyoctene, etc.), polyphenylenes (e.g., polyphenylene oxide, polyphenylene sulfide, polyphenylene ether sulfone, etc.), silicon containing polymers (e.g., polydimethyl siloxane, polycarbomethyl silane, etc.), polyurethanes, polyvinyls (e.g., polyvinyl butyral, polyvinyl alcohol, polyvinyl acetate, polystyrene, polymethylstyrene, polyvinyl chloride, polyvinyl pyrrolidone, polymethyl vinyl ether, polyethyl vinyl ether, polyvinyl methyl ketone, etc.), polyacetals, polyarylates, copolymers (e.g., polyethylene-co-vinyl acetate, polyethylene-co-acrylic acid, polybutylene terephthalate-co-polytetramethylene terephthalate, polylauryllactam-block-polytetrahydrofuran, etc.), and mixtures thereof.

In one embodiment of the invention, the matrix polymer is selected from at least one of polyphenylene sulfide (PPS), polyetheretherketone (PEEK), polyetherketone (PEK), polyphthalamide (PPA), polyetherketoneketone (PEKK), thermoplastic polyimide (TPI), high temperature nylon (HTN), polysulfone (PSU), polyethersulfone (PES), polyetherimide (PEI), and blends thereof.

Article of Manufacture—Pull Apart Device

A pull apart device can be formulated by combining the microcapsules of the invention with a releasing substrate. More particularly, a device can be fashioned of a first ply, which is polymeric, such as a polystyrene coated paper. A second ply can comprise polystyrene or a polystyrene blend or another polystyrene paper. Microcapsules are deposited with a binder onto an inside surface of the first ply. The capsules are adhered, optionally such as with an adhesive or binder, to the respective inside surfaces of the plies. The adhesive or binder, or a capsule coating bonds the overlying surfaces together. The bond between the top and bottom surfaces can be broken by separating the plies and in the process pulling the capsules apart sufficient to release the benefit agent, such as fragrances, antiseptic or lotion, or other benefit agent to release the contained material. A mixture of capsules or benefit agents can also be beneficially employed for multiple effects.

Article of Manufacture—Paints and Lacquers

Microcapsules according to the invention encapsulating benefit agents can usefully be combined with resinous binders to form lacquers and paints. In this manner fragrances, insecticides, biocides or oils can be incorporated into paints and lacquers.

Up to 2.5% by weight, or even up to 5%, or even up to 15% or even up to 30% by weight of encapsulated benefit agent, for example, can be incorporated into paint such as semi-gloss or flat Behr paint (commercial brand at Home Depot stores) under rigorous stirring (1800 rpm for 10 minutes).

The microcapsules for paints and lacquers are desirably of from 0.1 to 10 microns, preferably 0.1 to 5 microns.

Article of Manufacture—Nonwoven Web

A nonwoven web is constructed from polymeric fibers, such as synthetic fibers. Exemplary polymers for use in forming a nonwoven web may include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; and copolymers thereof. If desired, biodegradable polymers may also be employed.

Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth.

Monocomponent and/or multicomponent fibers may be used to form nonwoven web facing. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et at and U.S. Pat. No. 5,336,552 to Strack. et al., U.S. Pat. No. 5,108,820 to Kaneko et al., U.S. Pat. No. 4,795,668 to Kruege et al., U.S. Pat. No. 5,382,400 to Pike et al., U.S. Pat. No. 5,336,552 to Strack et al., and U.S. Pat. No. 6,200,669 to Marmon et al., which are incorporated herein by reference. Multicomponent fibers having various irregular shapes may also be formed, such as described in U.S. Pat. No. 5,277,976 to Hogle et al., U.S. Pat. No. 5,162,074 to Hills, U.S. Pat. No. 5,466,410 to Hills, U.S. Pat. No. 5,069,970 to Largman et al., and U.S. Pat. No. 5,057,368 to Largman et al., which are incorporated herein by reference.

When multiple layers of nonwoven webs are present, any of the nonwoven webs may include microcapsules throughout the web thickness. For example, one or all of the nonwoven webs in the nonwoven layer can include fragrance, oil or other benefit agent releasing microcapsules distributed throughout the the the web. Suitable multi-layered materials may include, for instance, spunbond/meltblown/spunbond (SMS) laminates and spunbond/meltblown (SM) laminates. Various examples of suitable SMS laminates are described in U.S. Pat. No. 4,041,203 to Brock et al.; U.S. Pat. No. 5,213,881 to Timmons et al.; U.S. Pat. No. 5,464,688 to Timmons et al.; U.S. Pat. No. 4,374,888 to Bornslaeger; U.S. Pat. No. 5,169,706 to Collier et al.; and U.S. Pat. No. 4,766,029 to Brock et al., which are incorporated herein by reference.

The web may also contain an additional fibrous component composite. Microcapsules can be incorporated in the composite or nonwoven, or both. For example, a nonwoven web may be entangled with another fibrous component using any of a variety of entanglement techniques known in the art (e.g., hydraulic, air, mechanical, etc.). In one embodiment, the nonwoven web is integrally entangled with cellulosic fibers using hydraulic entanglement. Hydraulically entangled nonwoven webs of staple length and continuous fibers are disclosed, for example, in U.S. Pat. No. 3,494,821 to Evans and U.S. Pat. No. 4,144,370 to Boulton, which are incorporated herein by. Hydraulically entangled composite nonwoven webs of a continuous fiber nonwoven web and a pulp layer are disclosed, for example, in U.S. Pat. No. 5,284,703 to Everhart et al. and U.S. Pat. No. 6,315,864 to Anderson et al., which are incorporated herein by reference.

Liquid Personal Care Compositions

Exemplary liquid rinse-off personal care compositions can include an aqueous carrier, which can be present at a level of from about 5% to about 95%, or from about 60% to about 85%. The aqueous carrier may comprise water, or a miscible mixture of water and organic solvent. Non-aqueous carrier materials can also be employed.

Such rinse-off personal care compositions can include one or more detersive surfactants. The detersive surfactant component can be included to provide cleaning performance to the product. The detersive surfactant component in turn comprises anionic detersive surfactant, zwitterionic or amphoteric detersive surfactant, or a combination thereof. A representative, non-limiting, list of anionic surfactants includes anionic detersive surfactants for use in the compositions can include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one example, the anionic surfactant can be sodium lauryl sulfate or sodium laureth sulfate. The concentration of the anionic surfactant component in the product can be sufficient to provide a desired cleaning and/or lather performance, and generally ranges from about 2% to about 50%.

Amphoteric detersive surfactants suitable for use in the rinse-off personal care compositions are well known in the art, and include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic detersive surfactants suitable for use in the rinse-off personal care compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

The liquid rinse off personal care composition can comprise one or more phases. Such personal care compositions can include a cleansing phase and/or a benefit phase (i.e., a single- or multi-phase composition). Each of a cleansing phase or a benefit phase can include various components. The cleansing phase and the benefit phase can be blended, separate, or a combination thereof. The cleansing phase and the benefit phase can also be patterned (e.g. striped).

The cleansing phase of a personal care composition can include at least one surfactant. The cleansing phase can be an aqueous structured surfactant phase and constitute from about 5% to about 20%, by weight of the personal care composition. Such a structured surfactant phase can include sodium trideceth(n) sulfate, hereinafter STnS, wherein n can define average moles of ethoxylation. n can range, for example, from about 0 to about 3; from about 0.5 to about 2.7, from about 1.1 to about 2.5, from about 1.8 to about 2.2, or n can be about 2. When n can be less than 3, STnS can provide improved stability, improved compatibility of benefit agents within the personal care compositions, and increased mildness of the personal care compositions as disclosed in U.S. Pre-Grant Publication No. 2010/009285 A1.

The cleansing phase can also comprise at least one of an amphoteric surfactant and a zwitterionic surfactant. Suitable amphoteric or zwitterionic surfactants (in addition to those cited herein) can include, for example, those described in U.S. Pat. Nos. 5,104,646 and 5,106,609.

A cleansing phase can comprise a structuring system. A structuring system can comprise, optionally, a non-ionic emulsifier, optionally, from about 0.05% to about 5%, by weight of the personal care composition, of an associative polymer; and an electrolyte.

The personal care composition can optionally be free of sodium lauryl sulfate, hereinafter SLS, and can comprise at least a 70% lamellar structure. However, the cleansing phase could comprise at least one surfactant, wherein the at least one surfactant includes SLS. Suitable examples of SLS are described in U.S. Pre-Grant Publication No. 2010/0322878 A1.

Rinse-off personal care compositions can also include a benefit phase. The benefit phase can be hydrophobic and/or anhydrous. The benefit phase can also be substantially free of surfactant. A benefit phase can also include a benefit agent. In particular, a benefit phase can comprise from about 0.1% to about 50% benefit agent by weight of the personal care composition. The benefit phase can alternatively comprise less benefit agent, for example, from about 0.5% to about 20% benefit agent, by weight of the personal care composition. Examples of suitable benefit agents can include petrolatum, glyceryl monooleate, mineral oil, natural oils, and mixtures thereof. Additional examples of benefit agents can include water insoluble or hydrophobic benefit agents. Other suitable benefit agents are described in U.S. Pre-Grant Publication No. 2012/0009285 A1.

Non-limiting examples of glycerides suitable for use as hydrophobic skin benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and combinations thereof.

Non-limiting examples of alkyl esters suitable for use as hydrophobic skin benefit agents herein can include isopropyl esters of fatty acids and long chain esters of long chain (i.e. C10-C24) fatty acids, e.g., cetyl ricinoleate, non-limiting examples of which can include isopropyl palmitate, isopropyl myristate, cetyl ricinoleate, and stearyl ricinoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of polyglycerin fatty acid esters suitable for use as hydrophobic skin benefit agents herein can include decaglyceryl distearate, decaglyceryl diisostearate, decaglyceryl monomyriate, decaglyceryl monolaurate, hexaglyceryl monooleate, and combinations thereof.

The rinse-off personal care composition can be applied by a variety of means, including by rubbing, wiping or dabbing with hands or fingers, or by means of an implement and/or delivery enhancement device. Non-limiting examples of implements include a sponge or sponge-tipped applicator, a mesh shower puff, a swab, a brush, a wipe (e.g., wash cloth), a loofah, and combinations thereof. Non-limiting examples of delivery enhancement devices include mechanical, electrical, ultrasonic and/or other energy devices. Employment of an implement or device can help delivery of the particulate antimicrobial agent to target regions, such as, for example, hair follicles and undulations that can exist in the underarm. The rinse-off care product can be sold together with such an implement or device. Alternatively, an implement or device can be sold separately but contain indicium to indicate usage with a rinse-off care product. Implements and delivery devices can employ replaceable portions (e.g., the skin interaction portions), which can be sold separately or sold together with the rinse-off care product in a kit.

Solid Personal Care Compositions

As noted herein, personal care compositions can take on numerous forms. One suitable form is that of a solid personal care composition. Solid compositions can take many forms like powder, pellets, bars, etc. These forms will generally be described herein as bar soap, but it should be understood that the solid composition could be in another form or shape. One example of a bar soap personal care composition can include from about 0.1% to about 35%, by weight of the personal care composition, of water, from about 45% to about 99%, by weight of the personal care composition, of soap, and from about 0.01% to about 5%, by weight of the personal care composition, of a particulate antimicrobial agent. Another suitable antimicrobial bar soap can include, for example, from about 0.1% to about 30%, by weight of the personal care composition, of water, from about 40% to about 99%, by weight of the personal care composition, of soap, and from about 0.25% to about 3%, by weight of the personal care composition, of a particulate antimicrobial agent.

Bar soap compositions can be referred to as conventional solid (i.e. non-flowing) bar soap compositions. Some bar soap composition can comprise convention soap, while others can contain synthetic surfactants, and still others can contain a mix of soap and synthetic surfactant. Bar compositions can include, for example, from about 0% to about 45% of a synthetic anionic surfactant. An example of a suitable conventional soap can include milled toilet bars that are unbuilt (i.e. include about 5% or less of a water-soluble surfactancy builder).

A personal care bar composition can include soap. By weight, the soap can be, for example, from about 45% to about 99%, or from about 50% to about 75%, by weight of the personal care composition. Such soaps can include a typical soap, i.e., an alkali metal or alkanol ammonium salt of an alkane- or alkene monocarboxylic acid. Sodium, magnesium, potassium, calcium, mono-, di- and tri-ethanol ammonium cations, or combinations thereof, can be suitable for a personal care composition. The soap included in a personal care composition can include sodium soaps or a combination of sodium soaps with from about 1% to about 25% ammonium, potassium, magnesium, calcium, or a mixture of these soaps. Additionally, the soap can be well-known alkali metal salts of alkanoic or alkenoic acids having from about 12 to about 22 carbon atoms or from about 12 to about 18 carbon atoms. Another suitable soap can be alkali metal carboxylates of alkyl or alkene hydrocarbons having from about 12 to about 22 carbon atoms. Additional suitable soap compositions are described in U.S. Pre-Grant Publication No. 2012/0219610 A1.

A personal care composition can also include soaps having a fatty acid. For example, one bar soap composition could contain from about 40% to about 95% of a soluble alkali metal soap of $C_8$-$C_{24}$ or $C_{10}$-$C_{20}$ fatty acids. The fatty acid can, for example, have a distribution of coconut oil that can provide a lower end of a broad molecular weight range or can have a fatty acid distribution of peanut or rapeseed oil, or their hydrogenated derivatives, which can provide an upper end of the broad molecular weight range. Other such compositions can include a fatty acid distribution of tallow and/or vegetable oil. The tallow can include fatty acid mixtures that can typically have an approximate carbon chain length distribution of 2.5% $C_{14}$, 29% $C_{16}$, 23% $C_{18}$, 2% palmitoleic, 41.5% oleic, and 3% linoleic. The tallow can also include other mixtures with a similar distribution, such as fatty acids derived from various animal tallows and/or lard. In one example, the tallow can also be hardened (i.e., hydrogenated) such that some or all unsaturated fatty acid moieties can be converted to saturated fatty acid moieties.

Suitable examples of vegetable oil include palm oil, coconut oil, palm kernel oil, palm oil stearine, soybean oil, and hydrogenated rice bran oil, or mixtures thereof, since such oils can be among more readily available fats. One example of a suitable coconut oil can include a proportion of fatty acids having at least 12 carbon atoms of about 85%. Such a proportion can be greater when mixtures of coconut oil and fats such as tallow, palm oil, or non-tropical nut oils or fats can be used where principle chain lengths can be $C_{16}$ and higher. The soap included in a personal care composition can be, for example, a sodium soap having a mixture of about 67-68% tallow, about 16-17% coconut oil, about 2% glycerin, and about 14% water.

Soap included in a personal care composition can also be unsaturated in accordance with commercially acceptable standards. For example, a soap included in a personal care composition can include from about 37% to about 45% unsaturated saponified material.

Soaps included in a personal care composition can be made, for example, by a classic kettle boiling process or modern continuous soap manufacturing processes wherein natural fats and oils such as tallow or coconut oil or their equivalents can be saponified with an alkali metal hydroxide using procedures well known to those skilled in the art. Soap can also be made by neutralizing fatty acids such as lauric ($C_{12}$), myristic ($C_{14}$), palmitic ($C_{16}$), or stearic ($C_{18}$) acids, with an alkali metal hydroxide or carbonate.

Soap included in a personal care composition could also be made by a continuous soap manufacturing process. The soap could be processed into soap noodles via a vacuum flash drying process. One example of a suitable soap noodle comprises about 67.2% tallow soap, about 16.8% coconut soap, about 2% glycerin, and about 14% water, by weight of the soap noodle. The soap noodles can then be utilized in a milling process to finalize a personal care composition.

Test Methods

Viscosity Test Method. Viscosity is measured using an AR 550 rheometer/viscometer from TA instruments (New Castle, Del., USA), using parallel steel plates of 40 mm diameter and a gap size of 500 μm. The high shear viscosity at 20 $s^{-1}$ is obtained from a logarithmic shear rate sweep from 0.1 $s^{-1}$ to 25 $s^{-1}$ in 3 minutes time at 21° C.

Test Method for Determining the Logarithm of the Octanol/Water Partition Coefficient (log P). The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Cleaning and/or Treatment Composition Examples

A series of cleaning and/or treatment compositions are prepared and evaluated as follows: the examples being designated with the letters CL followed by the sequence to distinguish from the microcapsule examples, noted above. In each example and table below, the amount of each ingredient is presented as a wt %.

Example AM1—Light Cleaning/Additive Composition. A liquid composition for very light cleaning or additive to the laundry process is prepared with microcapsules of the present invention by combining the microcapsules with the additional ingredients presented in Table 2.

TABLE 2

| Ingredients | Amount |
| --- | --- |
| Nonionic Surfactant (1) | 0-10 |
| Emulsifier (2) | 0-10 |
| Cationic surfactant | 0-10 |
| Anti-bac | 0-5 |
| Free (Neat) Perfume | 0-10 |
| Microcapsules (3) | 0-10 |
| Structurant | 0-0.3 |
| Aesthetics Dye | 0.015 |
| Water | Balance |

Example AM 2—Liquid Detergent Compositions. An HDL-Heavy Duty Liquid composition is prepared with microcapsules of the present invention by combining the microcapsules with the additional ingredients presented in Table 3. The exemplified space is meant to represent dilute to concentrated detergent products. The resulting detergent liquid product when used to wash articles of clothing is effective at freshening washed clothing.

TABLE 3

| Ingredient | % wt Active |
| --- | --- |
| Alkyl (ethoxy) sulfate (1) | 0-30 |
| Linear alkyl benzene sulfonic acid (2) | 0-30 |
| HSAS (3) | 0-30 |
| Nonionic Surfactant (4) | 0-15 |
| Amine Oxide | 0-8 |
| Citric Acid | 0-10 |
| Lactic Acid | 0-10 |
| $C_{12}$-$C_{10}$ Fatty Acid | 0-5 |
| Protease (55.3 mg/g) | 0-3 |
| Amylase (25.4 mg/g) | 0-2 |
| Borax | 0-5 |
| Calcium Formate | 0-0.5 |

TABLE 3-continued

| Ingredient | % wt Active |
|---|---|
| Polyethyleneimine 600, EO20 (5) | 0-5 |
| Polyethyleneimine 600, EO24, PO16 (6) | 0-5 |
| DTPA (7) | 0-5 |
| Optical Brightener (8) | 0-1 |
| NaOH | As needed |
| Na Cumene Sulfonate | 0-5 |
| Na Formate | 0-1 |
| MEA hydrogenated castor oil | 0-0.5 |
| Aesthetics Dye | 0-1.0 |
| Free (Neat) Perfume | 0-3.0 |
| Microcapsules (9) | 0-5 |
| Water and Solvent | To 100 |
| pH | 3.5-8.5 |

(1) Typically, the alkyl group has about 12 to about 18 carbons and with 0 to about 3 ethoxylate groups.
(2) Typically, the alkyl group has about 10 to about 16 carbons.
(3) HSAS is secondary alkyl sulfate, acid form
(4) Alkyl ethoxylate with about 12 to about 18 carbons and about 5 to about 9 moles ethoxylation.
(5) Polyethyleneimine at about 600 molecular weight reacted with about 20 moles of ethylene oxide.
(6) Polyethyleneimine at about 600 molecular weight reacted with about 24 moles of ethylene oxide and about 16 moles of propylene oxide.
(7) Select optical brighteners from one or more of the following, Brightener 14, Brightener 36, Brightener 49.
(8) Select chelant from one or a combination of the following non-limiting list DTPA diethylene triamine pentaacetic acid, Tiron ® is 4,5-Dihydroxy-1,3-benzenedisulfonic acid disodium salt monohydrate, EDTA ethylene diamine tetra acetate, HEDP 1-Hydroxyethylidene-1,1-diphosphonic Acid, Octapirox 1-Hydroxy-4-methyl-6-(2,4,4-trimethylpentyl)-2(1H)-pyridone Ethanolamine, EDDS Ethylenediamine-N,N'-disuccinic acid.
(9) Microcapsules made in accordance with the examples of the present specification Example AM3—Liquid Fabric Enhancer Composition. Examples of liquid fabric enhancer compositions are prepared with microcapsules of the present invention by combining the microcapsules of the present invention with the additional ingredients as presented in Table 4.

TABLE 4

| Ingredient | A | B | C | D |
|---|---|---|---|---|
| FSA[1] | 12 | 21 | 18 | 14 |
| Low MW alcohol | 1.95 | 3.0 | 3.0 | 2.28 |
| Structurant | 1.25[2] | NIL | 0.2[3] | NIL |
| Free (Neat) Perfume | 1.50 | 1.8 | 2.0 | 1.50 |
| Microcapsules[4] | 4.0 | 1.85 | 1.85 | 3.7 |
| Calcium Chloride | 0.10 | 0.12 | 0.1 | 0.45 |
| DTPA[6] | 0.005 | 0.005 | 0.005 | 0.005 |
| Preservative (ppm)[7] | 5 | 5 | 5 | 5 |
| Antifoam[8] | 0.015 | 0.15 | 0.11 | 0.011 |

TABLE 4-continued

| Ingredient | A | B | C | D |
|---|---|---|---|---|
| Polyethylene imines[9] | 0.15 | 0.05 | NIL | 0.1 |
| PDMS emulsion[10] | NIL | 0.5 | 1 | 2.0 |
| Dispersant[11] | NIL | NIL | 0.5 | 0.2 |
| Organosiloxane[12] | 5 | NIL | NIL | NIL |
| Front-end Stability Aid | 0.06[13] | 0.63[14] | 0.36[13] | 0.14[14] |
| Dye (parts per million ppm) | 40 | 11 | 30 | 40 |
| Ammonium Chloride | 0-0.1 | 0-0.1 | 0-0.1 | 0.10 |
| Hydrochloric Acid | 0.010 | 0.01 | 0.10 | 0.010 |
| Waler | Balance | Balance | Balance | Balance |

[1]N,N-di(tallowoyloxyethyl)-N,N-dimethylammonium chloride.
[2]Cationic high amylose maize starch-available from National Starch under the trade name HYLON VII ®.
[3]Cationic polymer available from BASF ® under the name Rheovis ® CDE.
[4]Microcapsules made in accordance with the examples of the present specification.
[5]Diethylene triamine pentaacetic acid.
[6]19% active aqueous solution of 1,2 Benzisothiazolin-3-one (BIT) in dipropylene glycol and water available from Dow Chemical under the trade name Koralone B-119.
[7]Silicone antifoam agent available from Dow Corning ® under the trade name DC2310.
[8]Polyethylene imines available from BASF under the trade name Lupasol ®.
[9]Polydimethylsiloxane emulsion from Dow Corning ® under the trade name DC346.
[10]Non-ionic such as TWEEN 20 ™ or cationic surfactant as Berol 648 and Ethoquad ® C 25 from Akzo Nobel.
[11]Organosiloxane polymer condensate made by reacting hexamethylenediisocyanate (HDI), and a, w silicone diol and 1,3-propanediamine, N'-(3-(dimethylamino)propyl)-N, N-dimethyl-Jeffcat Z130) or N-(3-dimethylaminopropyl)-N,Ndiisopropanolamine (Jeffcat ZR50) commercially available from Wacker Silicones, Munich, Germany.
[12]Fineoxocol ® 180 from Nissan Chemical Co.
[13]Isofol ® 16 from Sasol.
**For example, PGE Liquid fabric enhancer compositions in EXAMPLE AM3 are made by combining the molten fabric softener active with the front-end stability agent to form a first mixture. This first mixture is combined with water and hydrochloric acid using a high shear mixing device to form a second mixture. The adjunct ingredients are combined with the second mixture using low shear mixing to form the fabric enhancing formula.

Liquid fabric enhancer compositions in EXAMPLE AM3 are used by dosing 10 to 60 g of the formula into the rinse liquor for example via dispensing into a clothes washing machine. Clothes are dried on a line or in an automated clothes dryer. The fabrics treated with these formulas have improved feel and scent.

Example AM4—Liquid Fabric Enhancer Composition. Examples of liquid fabric enhancer compositions are prepared with microcapsules of the present invention by combining the microcapsules with the additional ingredients as presented in Table 5.

TABLE 5

| Ingredients | ☝ | A | B | C | D | E | F | G | H | I |
|---|---|---|---|---|---|---|---|---|---|---|
| DEEDMAC[1] | | 16 | 9 | 9 | 12 | 4 | NIL | NIL | NIL | NIL |
| Dialkyl esterdimethyl ammonium methyl sulfate[2] | | NIL | NIL | NIL | NIL | NIL | ? | 2.5 | 9 | 11 |
| HCL | | 0.02 | 0.02 | 0.01 | 0.01 | NIL | 0.01 | NIL | 0.01 | 0.01 |
| Fromic Acid | | 0.05 | 0.05 | 0.05 | 0.05 | 0.05 | 0.05 | 0.025 | 0.05 | 0.05 |
| Proxel ®[3] | | 0.02 | 0.02 | 0.02 | 0.02 | 0.02 | 0.02 | 0.02 | 0.02 | 0.02 |
| CaCl2 | | 1 | 0.3 | 0.3 | 0.4 | NIL | 0.3 | NIL | 0.1 | 0.1 |
| Antiforam MP10[4] | | 0.2 | 0.1 | 0.1 | 0.1 | 0.1 | 0.1 | 0.1 | 0.1 | 0.1 |
| Rheovis CDE ®[5] | | 0.1 | NIL | NIL | NIL | 0.4 | 0.1 | 0.2 | NIL | 0.2 |
| Flosoft ®[3] | | NIL | 0.1 | 0.1 | 0.05 | NIL | NIL | NIL | 0.3 | NIL |
| Bardac 2250 ®[7] | | NIL | NIL | 0.5 | NIL | NIL | NIL | NIL | NIL | 0.5 |
| NaHEDP[8] | | 0.03 | 0.03 | 0.03 | 0.03 | 0.03 | 0.03 | 0.03 | 0.03 | 0.03 |
| Genapol T680 ®[9] | | NIL | NIL | NIL | NIL | NIL | NIL | NIL | 0.6 | 0.8 |
| CAE10[10] | | NIL | 0.6 | NIL | NIL | NIL | NIL | NIL | NIL | NIL |
| Clycerol | | NIL | 10 | NIL | NIL | NIL | NIL | NIL | NIL | 5 |
| Perfume | | 0-2 | 0.1 | 0-1.5 | 0-3 | 0-2.3 | 0-1.5 | 0-3 | 0-0.8 | 0-0.5 |

TABLE 5-continued

| Ingredients | ✋ | A | B | C | D | E | F | G | H | I |
|---|---|---|---|---|---|---|---|---|---|---|
| Encapsulated perfume | | 0-0.25 | 0-0.5 | 0-1 | 0-0.6 | 0-1.5 | 0-3 | 0-0.5 | 0-1 | 0-5 |
| Water | | To 100 | To 100 | To 100 | To 100 | To 100 | To 100 | To 100 | To 100 | To 100 |

[1] 91% activity, 9% isopropanol, supplied by Evonik
[2] Reaction product of triethanolamine and alkyl and/or fatty acids followed by methylation.
[3] Proxel GXL, 20% activity, supplied by Lonza
[4] MP10, 8% activity, supplied by Dow Coming
[5] Rheovis CDE, supplied by BASF
[6] Flosoft 222, supplied by SNF
[7] Bardac 2250, 50% activity, supplied by Lonza
[8] 20% activity
[9] Genapol T680, supplied by Clariant
[10] C12-14 ALCHOLO ETHOXYLATE AE 10 (24E10)

Example AM5—Soluble Uni-Dose Heavy Duty Liquid Composition. Examples of Soluble Uni-dose heavy duty liquid composition are prepared with microcapsules of the present invention by combining the microcapsules with the additional ingredients as presented in Table 6. The resulting Unidose pouch product when used to wash articles of clothing is effective at freshening garments.

TABLE 6

| | A | B | C | D | E | F 3 compartments pouched product | | |
|---|---|---|---|---|---|---|---|---|
| Form | liquid | liquid | liquid | liquid | gel | liq | liq | liq |
| Compartment # | 1 | 1 | 1 | 1 | 1 | 1 | 2 | 3 |
| Dosage (g) | 36.0 | 38.0 | 32.0 | 36.0 | 40.0 | 34.0 | 25 | 35 |
| Alkylbenzene sulfonic acid | 14.5 | 13.8 | 16.0 | 14.5 | 13.5 | 14.5 | 20.0 | NIL |
| $C_{12-14}$ alkyl ehtoxy 3 sulfate | 8.5 | 16.4 | 10.0 | 8.5 | 15.0 | 8.5 | NIL | NIL |
| $C_{12-13}$ alkyl 3-ethoxylate | NIL | NIL | NIL | 13.0 | NIL | NIL | NIL | NIL |
| $C_{12-14}$ alkyl 7-ethoxylate | 12.5 | 9.0 | 14.0 | NIL | 4.0 | 12.5 | 17.0 | NIL |
| C12-18 Fatty acid | 14.5 | 8.5 | 16.0 | 15.0 | 7.2 | 14.5 | 13.0 | NIL |
| Citric acid | NIL | NIL | NIL | 2.0 | 4.1 | NIL | NIL | NIL |
| Enzymes | 0-3 | 0-3 | 0-3 | NIL | 0-3 | 0-3 | 0-3 | NIL |
| PAP granule[1] | NIL | NIL | NIL | NIL | NIL | NIL | NIL | 50.0 |
| Ethoxysulfated Hexamethylene Diamine Dimethyl Quat | NIL | 3.0 | NIL | NIL | NIL | NIL | 2.2 | NIL |

TABLE 6-continued

| | A | B | C | D | E | F 3 compartments pouched product | | |
|---|---|---|---|---|---|---|---|---|
| Ethoxylated Polyethylenimine | 4.0 | 1.0 | NIL | 4.0 | 3.0 | 2.0 | NIL | NIL |
| Hydroxyethane diphosphonic acid | 1.0 | 1.0 | NIL | NIL | 1.6 | 0.6 | 0.6 | NIL |
| Ethylene diamine tetra(methylene phosphonic) acid | NIL | NIL | NIL | 1.0 | NIL | NIL | NIL | NIL |
| Brightener | 0.2 | 0.2 | 0.3 | 0.3 | 0.2 | 0.2 | 0.2 | NIL |
| Polydimethyl Siloxane | NIL | NIL | 3.0 | NIL | NIL | NIL | NIL | NIL |
| Hueing dye[2] | NIL | NIL | NIL | NIL | NIL | NIL | 0.05 | NIL |
| Perfume | 0-3.0 | 0-3.0 | 0-3.0 | 0-3.0 | 0-3.0 | 0-3.0 | NIL | NIL |
| Microcapsules of the present invention | 0-5 | 0-5 | 0-5 | 0-5 | 0-5 | 0-5 | NIL | NIL |
| Water and minors | To 100% | | | | | | | |
| Buffers (sodium carbonate, monoethanolamine | To pH 8.0 | | | | | | | |
| Solvents (1,2 propanediol, ethanol), Sulfate | To 100% | | | | | | | |

[1] ε-Phthalimido-peroxy-hexanoic acid particles made by Solvay Chemicals International, Brussels, Belgium.

Example AM 6—Dish Cleaning Composition. Examples of Dish cleaning compositions are prepared with microcapsules of the present invention by combining the microcapsules with the additional ingredients presented in Table 7.

TABLE 7

| | EXAMPLES | | | | | | |
|---|---|---|---|---|---|---|---|
| | A | B | C | D | E | F | G |
| Alkyl $C_{10-14}$ Ethoxy Sulphate (AE0.6S) | 26.9 | NIL | NIL | 25.7 | NIL | 11.1 | 21.0 |
| Alkyl $C_{10-14}$ Ethoxy Sulphate (AE2S) | NIL | 18.7 | 26.9 | NIL | 18.7 | NIL | NIL |
| Sodium alkyl benzene sulfonate | NIL | 8.0 | NIL | NIL | NIL | NIL | NIL |
| Sodium paraffin sulfonate | NIL | NIL | NIL | NIL | 8.0 | NIL | NIL |
| C12-14 dimethyl amine oxide | 6.1 | NIL | NIL | 4.1 | NIL | 3.7 | 10.0 |
| Cocamido propyl betaine | NIL | 4.5 | 6.8 | 3.2 | 6.0 | NIL | NIL |
| C12-13 EO7 nonionic | NIL | NIL | NIL | NIL | NIL | 1.0 | 2.0 |
| Branched Nonionic: 3-propyl heptanol EO8 | 1.0 | 0.8 | NIL | NIL | NIL | NIL | 1.0 |
| PEI600-EO10-PO7 block polymer | NIL | NIL | 0.8 | NIL | NIL | 0.4 | 0.8 |
| Perfume | 0-2 | 0-2 | 0-2 | 0-2 | 0-2 | 0-2 | 0-2 |
| Perfume microcapsule of the present invention | 0-1 | 0-0.5 | 0-0.5 | 0-1.5 | 0-0.5 | 0-0.8 | 0-2 |

TABLE 7-continued

| | EXAMPLES | | | | | | |
|---|---|---|---|---|---|---|---|
| | A | B | C | D | E | F | G |
| Ethanol | 4.0 | 5.0 | 3.0 | 3.0 | 2.0 | NIL | 3.0 |
| Polypropylene glycol MW2000 | 1.1 | 0.8 | 1.1 | 1.1 | 1.1 | 0.5 | 1.1 |
| Sodium Chloride | 1.3 | 0.8 | 1.3 | 0.5 | 0.8 | 1.3 | 1.3 |
| Minors ® and water | | | to balance up to 100% | | | | |

Example AM7—Compositions for Use in Cleaning in an Automatic

Dishwashing Machine. Automatic dish washing compositions are prepared with microcapsules of the present invention by combining the microcapsules with the additional ingredients presented in Table 8. Some aspects of the present invention have at least one water soluble compartment, preferably composed of Monosol 660 mm M8630K Water Soluble Film. In other aspects of the present invention the unit dose composition has more than one compartment and at least one of the compartments comprises powder as in EXAMPLE AM7 A.

TABLE 8

| | % wt Active | | |
|---|---|---|---|
| Ingredients | A POWDER | B LIQUID | C LIQUID |
| Sodium sulfate | 0-15 | 2-7 | NIL |
| Soda ash | 20-50 | NIL | NIL |
| Zinc carbonate | NIL | 0.1-0.2 | NIL |
| Zinc sulfate | NIL | NIL | 0.3-0.7 |
| Sodium silicate | 0-2 | 3-15 | 1-2 |
| Sodium bicarbonate | NIL | NIL | 15-25 |
| Glutamic acid-N,N-diacetic acid, tetra sodium salt | NIL | NIL | 3-7 |
| Citric acid | NIL | NIL | 1-2 |
| NaOH (preferably low iron) | NIL | 0-1.5 | |
| Carboxylate polymer, GT101 | 2.5-7 | NIL | 1.25 |
| Plurafac SLF 180 | 0.2-1.5 | NIL | 0.25-0.6 |
| MDGA | 5-15 | NIL | NIL |
| Polyacrylate thickener Polygel DKP | NIL | 0.7-2.3 | NIL |
| Acrylic/sulfonic dispersant Acusol 588 | 2-10 | NIL | NIL |
| Acrylic acid polymer Acusol 425N | NIL | 1-3 | NIL |
| Sodium hypochlorite bleach | 0-30 | 0.3-1.5 | NIL |
| Ultimase | 0-2 | NIL | NIL |
| Stainzyme | 0-1 | NIL | NIL |
| Savinase Ultra 16XL | NIL | NIL | 0.2-0.5 |
| Termamyl Ultra 300 L | NIL | NIL | 0.1-0.15 |
| Calcium Chloride | NIL | NIL | 03-0.4 |
| Dipropylene Glycol | NIL | NIL | NIL |
| Nonionic Surfactant | NIL | 9-50 | NIL |
| Plurafac SLF 180 | NIL | 25-60 | NIL |
| Glycerine | NIL | 0-1 | NIL |
| Dye | NIL | 0-0.1 | NIL |
| Nitric acid | NIL | 0.005-0.05 | NIL |
| Preservative sodium benzoate | NIL | 0.25-0.8 | 0.2-0.8 |
| Perfume | 0-1 | 0-1 | 0-1 |
| Microcapsules of the present invention | 0-2 | 0-2 | 0-2 |
| Balance Water | To 100 | To 100 | To 100 |

Fatty acid has C12 to C14 alkyl groups and mixtures thereof Rheovis ® AT 120 is a methacrylate/acrylic acid copolymer.

Example AM8—Spray for Cleaning Hard Surfaces. A spray for cleaning hard surfaces is prepared with microcapsules of the present invention by combining the microcapsules with the additional ingredients presented in Table 9.

TABLE 9

| Ingredients | % wt Active |
|---|---|
| $C_{13-15}$ alkyl ethoxylate (30) | 0-0.5 |
| $C_{9-11}$ alkyl ethoxylate (8) | 0-0.5 |
| $C_{12/14}$ Amine-oxide | 0-3 |
| Banquat 4280-Z | 0-3 |
| Ethylene glycol monohexyl ether | 0-1 |
| Phenoxyethanol | 0-1 |
| Dense Soda ash | 0-0.3 |
| Pentasodium diethylene triamine (DTPA) | 0-0.4 |
| Tartaric acid | 0-0.1 |
| Dye | 0-1.2 |
| 1,2-Benzisothioazolin-3-one | 0-0.1 |
| Perfume | 0-1 |
| Microcapsules of the present invention | 0-0.5 |
| Balance Water | To 100 |

Solid Article of Manufacture Examples

Example AM9—Free Flowing Particles. Free flowing particles are prepared with microcapsules of the present invention by combining the microcapsules with the additional ingredients presented in Table 10.

TABLE 10

| | % wt Active | | | |
|---|---|---|---|---|
| | A | B | C | D |
| Ingredients | | | | |
| Polyethylene glycol | 70-99 | 0-20 | 0-29 | 0-40 |
| Clay | 0-29 | 0-20 | 0-20 | 0-10 |
| NaCl | 0-29 | 50-99 | 0-29 | 0-40 |
| Na2SO4 | 0-10 | 0-10 | 0-10 | 0-5 |
| Urea | 0-29 | 0-29 | 0-99 | 0-40 |
| Polysaccharide | 0-29 | 0-29 | 0-29 | 0-5 |
| Zeolite | 0-29 | 0-29 | 0-29 | 0-5 |
| Plasticizers/ Solvents | | | | |
| Starch/Zeolite | 049 | 0-29 | 0-29 | 0-5 |
| Silica | 0-5 | 0-5 | 0-5 | 0-5 |
| Metal oxide | 0-29 | 0-29 | 0-29 | 0-29 |
| Metal catalyst | 0.001-0.5 | 0.001-0.5 | 0.001-0.5 | 0.001-0.5 |
| Opacifier | 0-5 | 0-5 | 0-1 | 0-1 |
| Water | 0-29 | 0-2 | 0-5 | 0-5 |
| Perfume | 0-5 | 0-5 | 0-5 | 0-5 |
| Microcapsules made in accordance with the examples of the present specification | 0-10 | 0-4.5 | 0-3 | 0-7.5 |

Example AM10—Spray-Dried Laundry Detergent Powder Composition.

Spray-dried laundry detergent powder compositions are prepared with microcapsules of the present invention by combining the microcapsules with the additional ingredients as presented in Table 11.

TABLE 11

| Ingredients | wt % Active Slurry | | | |
| --- | --- | --- | --- | --- |
| | A | B | C | D |
| Linear alkyl benzene sulfonate | 10.6 | 15.8 | 21.3 | 35.7 |
| Acrylate/maleate copolymer | 4.6 | 6.8 | 9.4 | 14.2 |
| Ethylenediame disuccinic acid and/or Hydroxyethane dimethylene phosphonic acid | 1.4 | 2.1 | 1.7 | 2.9 |
| Sodium carbonate | 19.4 | 26.5 | 18.8 | 29.9 |
| Sodium sulfate | 28.6 | 42.4 | — | — |
| Carboxy methyl cellulose polymer | — | — | 4.3 | 7.1 |
| Carboxy methyl cellulose polymer | — | — | 4.3 | 7.1 |
| Miscellaneous, such as magnesium sulfate, brightener and one or more stabilizers | 1.4 | 2.2 | 2.5 | 4.2 |
| Perfume | 0-3 | 0-2 | 0-2 | 0-3 |
| Microcapules made in accordance with the examples of the present specification | 0-5 | 0-5 | 0-5 | 0-5 |
| Water | Balance | Balance | Balance | Balance |

A first spray-dried laundry detergent powder is formed from an aqueous slurry, slurry A from Table 11, which is prepared having a moisture content of 34.0%. Any ingredient added above in liquid form is heated to 70° C., such that the aqueous slurry is never at a temperature below 70° C. At the end of preparation, the aqueous slurry is heated to 80° C. and pumped under pressure ($5 \times 10^6$ $Nm^{-2}$) into a counter current spray-drying tower with an air inlet temperature of from 290° C. The aqueous slurry is atomized, and the atomized slurry is dried to produce a solid mixture, which is then cooled and sieved to remove oversize material (>1.8 mm) to form a spray-dried powder, which is free-flowing. Fine material (<0.15 mm) is elutriated with the exhaust the exhaust air in the spray-drying tower and collected in a post tower containment system. The spray-dried powder has a moisture content of 2.0 wt %, a bulk density of 310 WI and a particle size distribution such that greater than 90 wt % of the spray-dried powder has a particle size of from 150 to 710 micrometers. The composition of the spray-dried powder A is listed in the Table 11. Perfume and microcapsules are sprayed onto the composition following the spray dry procedure.

A second spray-dried laundry detergent powder is formed from an aqueous slurry, slurry B from Table 11, having a moisture content of 42.0%. Any ingredient added above in liquid form is heated to 70° C., such that the aqueous slurry is never at a temperature below 70° C. At the end of preparation, the aqueous slurry is heated to 85° C. and pumped under pressure (from $6.5 \times 10^6$ $Nm^{-2}$), into a counter current spray-drying tower with an air inlet temperature of from 275° C. The aqueous slurry is atomized, and the atomized slurry is dried to produce a solid mixture, which is then cooled and sieved to remove oversize material (>1.8 mm) to form a spray-dried powder B, which is free-flowing. Fine material (<0.15 mm) is elutriated with the exhaust the exhaust air in the spray-drying tower and collected in a post tower containment system. The spray-dried powder has a moisture content of 3.0 wt %, a bulk density of 250 g/l and a particle size distribution such that greater than 90 wt %) of the spray-dried powder has a particle size of from 150 to 710 micrometers. The composition of the spray-dried powder is given in Table 11. Perfume and microcapsules are sprayed onto the composition after the spray dry process.

Example AM11—Freshening Composition. Liquid fabric spray fabric freshening compositions are prepared with microcapsules of the present invention by combining the microcapsules with the additional ingredients as presented in Table 12. The resulting fabric refreshing spray product when used to treat fabric surfaces is effective at freshening a treated fabric.

TABLE 12

| Ingredient | wt % Active | | | | |
| --- | --- | --- | --- | --- | --- |
| | A | B | C | D | E |
| Deionized Water | Balance | Balance | Balance | Balance | Balance |
| Ethanol | 3.0 | 3.0 | 3.0 | 3.0 | 3.0 |
| Lupasol HF[1] | NIL | NIL | NIL | NIL | NIL |
| Hydroxypropyl b-CD | NIL | NIL | NIL | NIL | NIL |
| Diethylene Glycol | NIL | NIL | NIL | NIL | NIL |
| Silwet L-7600 | 0.1 | 0.1 | 0.1 | 0.100 | 0.100 |
| Basophor EL60[2] | NIL | 0.05 | 0.05 | 0.05 | 0.05 |
| Maleic Acid and/or Citric Acid[3] | As seeded | As needed | As needed | As needed | As needed |
| Kotalone B-119 | 0.015 | 0.015 | 0.015 | 0.015 | 0.015 |
| Hydroxypropyl β-cyclodextrin | NIL | NIL | NIL | NIL | NIL |
| Sodium Hydroxide[3] | As needed | As needed | As needed | As needed | As needed |
| Microcapsules made in accordance with the examples of the present specification | 1 | 2 | 0.1 | 5 | 0.05 |
| Fragrance | 0 | 0 | 0 | 0 | 0 |
| Target pH | 6.8 | 6.8 | 6.8 | 6.8 | 6.8 |
| Total | 100 | 100 | 100 | 100 | 100 |

Example AM12—Dryer Added Fabric Softener Sheet Composition. A series of dryer added fabric softener sheet compositions are prepared with microcapsules of the present invention by combining the microcapsules with the additional ingredients as presented in Table 13. The compositions A-D of this example are mixed homogeneously and impregnated onto a non-woven polyester sheet having dimensions of about 6% in×12" (about 17.1 cm×30.5 cm) and weighing about 1 gram. The resulting dryer added fabric softener sheet product when added to an automatic dryer is effective at softening, freshening and reducing the static on clothing that contact the sheet.

TABLE 13

| Ingredient | A Wt % Active | B Wt % Active | C Wt % Active | D Wt % Active |
| --- | --- | --- | --- | --- |
| DEQA[1] | 0-50 | 50 | — | — |
| DEQA[2] | 0-50 | — | — | 30 |
| DTDMAMS[3] | 0-50 | — | 50 | — |
| 7018FA[4] | 0-50 | — | 50 | — |
| TS-20[5] | 0-15 | — | — | 15 |
| SMS[6] | 0-15 | — | — | 15 |
| SDASA[7] | 0-19 | 25 | — | 19 |
| TPED[8] | — | 3 | — | — |
| Complex[9] | 0-16.5 | 16.5 | — | 8.0 |
| Clay[10] | Balance | Balance | Balance | Balance |
| Free (Neat) Perfume | 0-4 | 0-1.5 | 0-3 | 0-1.5 |
| Microcapsules[11] | 0-4 | 0-4 | 0-2 | 0-2 |
| Active Weight (g/sheet) | 2.4 | 2.4 | 1.9 | 2.4 |

[1]DEQA[1]: Di(soft tallowoyloxyethyl)dimethylammonium methyl sulfate with 25% > 7018 FA, as described below, as solvent
[2]DEQA[2]: Di(soft tallowoyloxyethyl)hydroxyethylmethylammoniun methyl sulfate with 18% partially hydrogenated tallow fatty acid solvent
[3]DTDMAMS: Di(hydrogenated tallowalkyl)dimethylammonium methyl sulfate
[4]7018FA: 70:30 Stearic Acid:Palmitic Acid (IV = 0) Industrene 7018 sofa by Witco
[5]TS-20: Polyoxyethylene-20 Sorbitan Tristearate (Glycosperse TS-20, sofa by Lonza
[6]SMS: Sorbitan Mono Stearate
[7]SDASA: 1:2 ratio of stearyl dimethyl amine:triple pressed stearic acid
[8]TPED: N,N,N',N'-Tetrakis(2-hydroxypropyl)ethylenediamine (Quadrol, sold by BASF)
[9]Complex: Beta-Cyclodextrin/Perfume Complex
[10]Clay: Calcium Bentonite Clay (Bentonite L sold by Southern Clay Products Free (Neat) Perfume
[11]Microcapsules made in accordance with the examples of the present specification Examples AM13-AM15—Absorbent Articles Example AM13—Pads for Menstrual Odor Control. The microcapsules of the present invention are added into the core of a menstrual pad. Optionally, a neat fragrance is preferably added beneath the core of the article.

Example AM14—Heavy Adult Incontinence Pants for Urine Odor Control. The microcapsules of the present invention are added into the core of adult Incontinence underwear product. Optionally, a neat fragrance is preferably added beneath the core of the article.

Example AM15—Diapers for Odor Control. The microcapsules of the present invention are added into the core of a baby diaper. Optionally, a neat fragrance is preferably added beneath the core of the article.

Examples AM16-AM17—Personal Care Compositions.

Example AM16—Body Wash. Body Wash compositions are prepared with microcapsules of the present invention by combining the microcapsules with the additional ingredients as presented in Table 14.

TABLE 14

| Body Wash | A | B | C |
|---|---|---|---|
| Sodium Laureth-3 Sulfide (as 28% active) | 27.85% | 27.85% | 27.85% |
| Water | Q.S. | Q.S. | Q.S. |
| Sodium Lauryl Sulfate (as 29% active) | 10.34 | 10.34 | 10.34 |
| Cocamidopropyl Betaine B (30% active) | 4.01 | 4.01 | 4.01 |
| Citric Acid | 0.18 | 0.18 | 0.18 |
| Sodium Benzoate | 0.3 | 0.3 | 0.3 |
| Disodium EDTA | 0.12 | 0.12 | 0.12 |
| Methylchloroisothiazolinone/ Methylisothiazolinone | 0.04 | 0.04 | 0.04 |
| Sodium Chloride | 2.35 | 1.7 | 1.6 |
| Neat Perfume | 1.25 | 1 | 2 |
| Microcapsafes made in accordance with the examples of the present specification | 0.25 | 0.175 | 0.25 |

QS—indicates that this material is used to bring the total to 100%

Example AM17—Shampoos. Shampoo compositions are prepared with microcapsules of the present invention by combining the microcapsules with the additional ingredients as presented in Table 15.

TABLE 15

| Ingredient | A | B Wt % | C | D | E | F |
|---|---|---|---|---|---|---|
| Ammonium Laureth Sulfate[1] | 14.1 | 14.1 | 14.1 | 14.1 | 14.1 | 14.1 |
| Ammonium Lauryl Sulfate[2] | 3.1 | 3.1 | 3.1 | 3.1 | 3.1 | 3.1 |
| Ammonium Xylenesulfonate[3] | 0.45 | 0.45 | 0.45 | 0.45 | 0.45 | 0.45 |
| TWEEN 60[4] | 3.0 | 3.0 | 3.0 | 3.0 | 3.0 | 3.0 |
| Polyquaternium-10[5] | 0.35 | 0.35 | 0.35 | 0.35 | 0.35 | 0.35 |
| Cetrimonium Chloride[6] | 0.5 | 0.5 | 0.5 | 0.5 | 0.5 | 0.5 |
| Selenium Sulfide[7] | 1.0 | 1.0 | 1.0 | 1.0 | 0.2 | 0.2 |
| Dimethicone[8] | 0.60 | 0.60 | 0.60 | 0.60 | 0.60 | 0.60 |
| Ethylene Glycol Distearate[9] | 3.0 | 3.0 | 3.0 | 3.0 | 3.0 | 3.0 |
| Cocamide MEA[10] | 3.0 | 3.0 | 3.0 | 3.0 | 3.0 | 3.0 |
| Zinc Pyrithione[11] | — | 0.2 | 0.2 | — | 1.0 | 1.0 |
| Zinc Carbonate[12] | — | — | 1.61 | — | — | 1.61 |
| Neat Fragrance | 1.1 | 0.75 | 0.75 | 0.65 | 0.85 | 1.0 |
| Microcapsules made in accordance with the examples of the present specification | 0.25 | 0.25 | 0.175 | 0.175 | 0.175 | 0.175 |
| Cetyl Alcohol[13] | 0.42 | 0.42 | 0.42 | 0.42 | 0.42 | 0.42 |
| DMDM Hydantoin | 0.40 | 0.40 | 0.40 | 0.40 | 0.40 | 0.40 |
| Sodium Chloride | 0.30 | 0.30 | 0.30 | 0.30 | 0.30 | 0.30 |
| Stearyl Alcohol[14] | 0.20 | 0.20 | 0.20 | 0.20 | 0.20 | 0.20 |
| Hydroxypropyl Methylcellulose[15] | 0.02 | 0.02 | 0.02 | 0.02 | 0.02 | 0.02 |
| Water | Q.S. | Q.S. | Q.S. | Q.S. | Q.S. | Q.S. |

[1]Ammonium Laureth Sulfate at 25% active, supplier: P&G

[2]Ammonium Lauryl Sulfate at 25% active, supplier: P&G

[3]Ammonium Xylene Sulfonate 40% active, supplier: Stepan

[4]Polysorbate 60, supplier: Croda

[5]UCARE Polymer LR400, supplier-Dow Chemical

[6]cetrimonium chloride, supplier-Croda

[7]Selenium disulfide, supplier Eskay

[8]Viscasil 330M from Momentive Performance Materials with a viscosity of 330,000 cSt (centistokes).

[9]Ethylene Glycol Disterate, supplier: Stepan

[10]Ninol COMF from the Stepan Company

[11]Zinc Pyrithione, supplier Lonza

[12]Zinc Carbonate Basic, supplier Pan Continental Chemical

[13]Cetyl Alcohol, supplier P&G

[14]Stearyl Alcohol, supplier P&G

[15]Methocel, supplier Dow Chemical

Examples AM18-AM20—Antiperspirant and/or Deodorant Compositions

Example AM18—Deodorants. Deodorants are prepared with microcapsules of the present invention by combining the microcapsules with the additional ingredients as presented in Table 16.

TABLE 16

| Ingredient | A | B | C | D | E |
|---|---|---|---|---|---|
| Product Form | Solid Deodorant | Solid Deodorant | Solid Deodorant | Solid Deodorant | Aerosol Deodorant or Body Spray |
| dipropylene glycol | 48 | 48 | 20 | 30 | 20 |
| propylene glycol | 19.3 | 19.3 | 22 | — | — |
| tripopylene glycol | — | — | 25 | — | — |
| Glycerine | — | — | — | 10 | — |
| PEG-8 | — | — | — | 20 | — |
| Propylene Glycol 3 Myristyl Ether | 1.4 | 1.4 | — | — | — |
| ethanol | — | — | — | — | QS |
| Water | QS | QS | QS | QS | — |
| sodium stearate | 5.4 | 5.4 | 5.5 | 5.5 | — |
| tetra sodium EDTA | 0.5 | 0.5 | 0.05 | 0.05 | — |
| sodium hydroxide | — | — | 0.94 | 0.04 | — |
| triclosan | — | — | 0.3 | 0.3 | — |
| Neat Perfume | 2.8 | 2.8 | 2 | 1.5 | 1.5 |
| Microcapsules made in accordance with the examples of the present specification | 3 | 0.7 | 1.0 | 0.5 | 0.35 |
| Blue 1 | 0.0009 | 0.0009 | — | — | — |
| Propellant (1,1 difluoroethane) | — | — | — | — | 40 |

QS—Indicates that this material is used to bring the total to 100%.

Example AM19—Antiperspirants. Antiperspirant compositions are prepared with microcapsules of the present invention by combining the microcapsules with the additional ingredients as presented in Table 17.

TABLE 17

| Ingredient | Form | | | | | |
|---|---|---|---|---|---|---|
| | Invisible Solid A | Invisible Solid B | Invisible Solid C | Soft Solid D | Soft Solid E | Soft Solid F |
| Aluminum Zirconium Trichlorohydrex Glycine Powder | 24 | 24 | 24 | 26.5 | 26.5 | 26.5 |
| Cyclopentasiloxane | Q.S. | Q.S. | Q.S. | Q.S. | Q.S. | Q.S. |
| Dimethicone | — | — | — | 5 | 5 | 5 |
| CO-1897 Stearyl Alcohol NF | 14 | 14 | 14 | — | — | — |
| Hydrogenated Castor Oil MP80 Deodorized | 3.85 | 3.85 | 3.85 | — | — | — |
| Behenyl Alcohol | 0.2 | 0.2 | 0.2 | — | — | — |
| Tribehenin | — | — | — | 4.5 | 4.5 | 4.5 |
| C 18-36 acid triglyceride | — | — | — | 1.125 | 1.125 | 1.125 |
| C 12-15 Alkyl Benzoate | 9.5 | 9.5 | 5 | — | — | — |
| PPG-14 Butyl Ether | 6.5 | 6.5 | — | 0.5 | 0.5 | 0.5 |
| Phenyl Trimethicone | 3 | — | 3 | — | — | — |
| White Petrolatum | 3 | — | — | 3 | 3 | 3 |
| Mineral Oil | 1.0 | 1.0 | 1.0 | — | — | — |
| Free (Neat) Perfume | 1.0 | 0.75 | 2.0 | 0.75 | 1.0 | 1.25 |
| Microcapsules made in accordance with the examples of the present specification | 0.25 | 3 | 0.35 | 0.175 | 0.25 | 0.1 |
| Beta-Cyclodextrin complexed with Malodor reducing composition | — | 3.0 | — | — | — | 3.0 |
| Tacl Imperial 250 USP | 3.0 | 3.0 | 3.0 | — | — | — |

QS - indicates that this material is used to bring the total to 100%.

Example AM20—Clear Gel Antiperspirant. Clear gel antiperspirants are prepared with microcapsules of the present invention by combining the microcapsules with the additional ingredients as presented in Table 18.

TABLE 18

|  | 3,1 Clear Gel Antiperspirant | 3.2 Clear Gel Antiperspirant | 3.3 Clear Gel Antiperspirant | 3.4 Clear Gel Antiperspirant | 3.5 Clear Gel Antiperspirant |
|---|---|---|---|---|---|
| Aluminum Zirconium Octachlorohydrex Gly | 20 | 18.5 | 20 | 18 | 10 |
| Water | Q.S | Q.S. | Q.S. | Q.S. | Q.S. |
| Ethanol | 5.5 | 8 | 6 | 6.5 | 5 |
| Propylene Glycol | 5.3 | 5 | 7 | 5.5 | 8 |
| DC 5225c-Cyclopentasiloxane & PEG/PPG-18/18 Dimethicone | 7.8 | 0 | 6.5 | 7 | 8 |
| Dimethicone | 5.6 | 4.5 | 5.8 | 5 | 4.1 |
| Cyclopentasiloxane | 2.6 | 3 | 1 | 3 | 2.5 |
| Free (Neat) Perfume | 1.0 | 0.75 | 2.0 | 0.75 | 1.0 |
| Microcapsules made in accordance with the examples of the present specification | 0.25 |  | 0.35 | 0.175 | 0.25 |

QS—indicates that this material is used to bring the total to 100%.

Example AM21—Matrix Polymer. Compositions comprising 10 wt % microcapsules in General Electric PET (Valox PET 962) and PEEK (Victrix P151) as the polymer matrix material can be prepared, melt-blending microcapsules in the composition. Oil capsules are incorporated in PET pellets, Example AM22—Matrix Polymer. Microcapsules in quantity from 10 to 30 wt % are added to General Electric PEI (Ultem PEI 1010 resin) composition via a side feeder of a Werner & Pfleiderer extruder (2 holes, two 2 lobs screws, and 9 barrels). PEI is added at the throat feeder.

Example AM23—Carrier Polymer. Up to 30 wt % of microcapsules are first incorporated into PET as a carrier polymer, with the melt blending at a temperature of about 260° C. Microcapsules are added to the extruder via a side feeder in a dry-blend with the PET carrier polymer (90% PET, 10% microcapsules).

For avoidance of doubt and to preclude any unintentional omission of an embodiment, it is to be appreciated that the present teaching also pertains to and by this reference incorporates any and all articles of manufacture and methods of making such articles containing or made using, respectively, the microcapsules embraced by the appended claims as well as the microcapsules resulting from the methods of the appended claims in combination with at least adjunct material. In general, these compositions and methods will contain or employ, as appropriate, a sufficient amount of said microcapsules to provide, based on the total article of manufacture weight, said article with from 0.001% to about 25%, or even to about 40%, preferably from about 0.01% to about 10%, more preferably from about 0.05% to about 5%, most preferably from about 0.1% to about 0.5% of said microcapsules.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

Although the process and prepared microcapsules of the present specification as well as various articles of manufacture including commercial, industrial and consumer products containing/comprising the same have been described with respect to specific embodiments and examples, it should be appreciated that the present teachings are not limited thereto and other embodiments utilizing the concepts expressed herein are intended and contemplated without departing from the scope of the present teaching as intended in the true spirit and scope of the invention. It is therefore intended any and all modifications, variations, or equivalents that fall within the spirit and scope of the underlying principles are within the scope of this invention and are covered by the appended claims.

Uses of singular terms such as "a" and "an" are intended to cover both the singular and the plural, unless otherwise indicated herein or clearly contradicted by context. The terms "comprising," "having," "including," and "containing" are to be construed as open-ended terms. All references, including publications, patent applications, and patents, cited herein are hereby incorporated by reference. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims.

What is claimed is:

1. An article of manufacture made by a process comprising combining an adjunct material and microcapsules, the microcapsules comprising a core and a shell surrounding the core, the microcapsules formed by a process comprising:

forming a water phase by hydrolyzing chitosan in an aqueous acidic medium at a pH of from 5.5 to 6.5 and a temperature of at least 40° C. for at least one hour;

forming an oil phase comprising dissolving together at least one benefit agent and at least one polyisocyanate, optionally with an added oil;

forming an emulsion by mixing under high shear agitation the water phase and the oil phase into an excess of the water phase, thereby forming droplets of the oil phase and benefit agent dispersed in the water phase;

curing the emulsion by heating to at least 40° C., for a time sufficient to form a shell at an interface of the droplets with the water phase, the shell comprising the reaction product of the polyisocyanate and hydrolyzed chitosan, and the shell surrounding the core comprising the droplets of the oil phase and benefit agent, wherein the weight percent of chitosan in the shell is from 25 wt. % to 90 wt. % and wherein the core is from 0.01 to 99 weight percent of the microcapsule.

2. The article of manufacture according to claim 1 wherein the adjunct material is selected from the group consisting of a carrier, a binder, an adhesive, a structurant, a surfactant, and a deposition aid.

3. The article of manufacture according to claim 1 wherein the article of manufacture comprises a consumer product.

4. The article of manufacture according to claim 1 wherein the article of manufacture is selected from the group consisting of a soap, a surface cleaner, a laundry detergent, a fabric softener, a shampoo, a textile, a paper towel, an adhesive, a wipe, a diaper, a feminine hygiene product, a facial tissue, a pharmaceutical, a napkin, a deodorant, a heat sink, a foam, a pillow, a mattress, bedding, a cushion, a cosmetic, a medical device, packaging, an agricultural product, a cooling fluid, a wallboard, and an insulation.

5. The article of manufacture according to claim 1 wherein the chitosan in the hydrolyzing step is deacetylated to at least 75%.

6. The article of manufacture according to claim 1 wherein the chitosan in the hydrolyzing step is depolymerized to an average size of 95 kDa or less.

7. The article of manufacture according to claim 1 wherein the shell formed is a chitosan polyurea, having a chitosan content of at least 50 wt % based on the weight of the shell.

8. The article of manufacture according to claim 1 wherein the microcapsules comprises an aqueous slurry having residual hydrolyzed chitosan in the slurry.

9. The article of manufacture according to claim 8 wherein the aqueous slurry is spray dried, forming microcapsules overcoated with a layer of residual hydrolyzed chitosan deposited onto the microcapsules from the slurry.

10. The article of manufacture according to claim 1 wherein the polyisocyanate is selected from the group consisting of a polyisocyanurate of toluene diisocyanate, a trimethylol propane adduct of toluene diisocyanate and a trimethylol propane adduct of xylylene diisocyanate, methylene diphenyl isocyanate, toluene diisocyanate, tetramethylxylidene diisocyanate, naphthalene-1,5-diisocyanate, and phenylene diisocyanate.

11. The article of manufacture according to claim 1 wherein the microcapsules are dried, and fracture upon drying, thereby releasing the core.

12. An article of manufacture comprising an adjunct material and a core-shell microcapsule, the core comprising a benefit agent, the shell comprising a polyurea resin comprising the reaction product of a polyisocyanate and a chitosan, wherein the chitosan is first hydrolyzed in an acidic medium at a pH of from 5.5 to 6.5, and a temperature of at least 40° C. for at least one hour;

wherein the weight percent of chitosan in the shell is from 25 wt. % to 90 wt. %, chitosan, wherein the microcapsules have a free oil of from 0.043 to 7.35%, wherein the core is from 0.01 to 99 weight percent of the microcapsule, and, wherein the shell when measured according to test method OECD 301B has a value for percent degradability of at least 60% at 28 days.

13. The article of manufacture according to claim 12 wherein the microcapsules rupture upon drying, releasing the benefit agent.

14. The article of manufacture according to claim 12, the shell comprising 1 to 15 percent by weight of the core-shell microcapsule.

15. The article of manufacture according to claim 12 wherein the polyisocyanate is selected from the group consisting of a polyisocyanurate of toluene diisocyanate, a trimethylol propane adduct of toluene diisocyanate, a trimethylol propane adduct of xylylene diisocyanate, methylene diphenyl isocyanate, toluene diisocyanate, tetramethylxylidene diisocyanate, naphthalene-1,5-diisocyanate, and phenylene diisocyanate.

16. The article of manufacture according to claim 15 wherein the shell when measured according to test method OECD 301B has a value for percent degradability of at least 50% at 20 days.

17. The article of manufacture according to claim 12 wherein the chitosan has a degree of deacetylation of at least 50%.

18. The article of manufacture according to claim 12 wherein the core-shell microcapsule has a ratio of core to shell up to 99:1, on the basis of weight.

19. The article of manufacture according to claim 12 wherein the benefit agent is selected from the group consisting of perfume, fragrance, agricultural active, phase change material, essential oil, lubricant, colorant, preservative, antimicrobial active, antifungal active, herbicide, antiviral active, antiseptic active, antioxidant, biological active, deodorant, emollient, humectant, exfoliant, ultraviolet absorbing agent, corrosion inhibitor, silicone oil, wax, bleach particle, fabric conditioner, malodor reducing agent, dye, optical brightener, antiperspirant active and mixture thereof.

20. The article of manufacture according to claim 12 wherein the core-shell microcapsules have a mean particle size of from 1 to 100 microns.

21. The article of manufacture according to claim 12 wherein the microcapsule is cationic.

22. The article of manufacture according to claim 12 wherein the article of manufacture is selected from the group consisting of a soap, a surface cleaner, a laundry detergent, a fabric softener, a shampoo, a textile, a paper towel, an adhesive, a wipe, a diaper, a feminine hygiene product, a facial tissue, a pharmaceutical, a napkin, a deodorant, a heat sink, a foam, a pillow, a mattress, bedding, a cushion, a cosmetic, a medical device, packaging, an agricultural product, a cooling fluid, a wallboard, and an insulation.

23. The article of manufacture according to claim 12 wherein the microcapsule has a zeta potential of at least 15 mV at a pH of 4.5.

\* \* \* \* \*